United States Patent [19]
Demorest et al.

[11] Patent Number: 5,578,179
[45] Date of Patent: Nov. 26, 1996

[54] METHOD AND SILICATE COMPOSITION FOR CONDITIONING SILICA SURFACES

[75] Inventors: David M. Demorest, Scotts Valley; Stephen E. Moring, Moss Beach; Claudia Chiesa, Palo Alto, all of Calif.

[73] Assignee: The Perkin-Elmer Corporation, Foster City, Calif.

[21] Appl. No.: 501,674

[22] Filed: Jul. 12, 1995

[51] Int. Cl.[6] ................................................ G01N 27/26
[52] U.S. Cl. .................................... 204/451; 204/454
[58] Field of Search .................................. 204/451, 454; 536/25.4; 530/415; 935/19, 20, 21

[56] References Cited

U.S. PATENT DOCUMENTS 4,781,982  11/1988  Musselman et al. ................... 428/403

*Primary Examiner*—Arun S. Phasge
*Attorney, Agent, or Firm*—Vincent M. Powers

[57] ABSTRACT

Disclosed is a method for increasing the electro-osmotic flow rate available for a silica surface. In the method, there is provided an electrophoretic channel which is defined by one or more silica surfaces. The surface(s) are contacted with an alkaline aqueous solution containing a solubilized silicate-monovalent metal complex in an amount effective to increase the acidity of the silica surface(s), as evidenced by a reduction in the average bulk pKa of the surface(s). The achieved increase in acidity is greater than would be obtained using an otherwise identical solution lacking said silicate. In one preferred embodiment, the monovalent metal used in the solution is $Li^+$, $Na^+$, or $K^+$. Also disclosed is a method for increasing the acidity of a silica surface, by contacting the surface with an alkaline aqueous solution of the type noted above.

18 Claims, 11 Drawing Sheets

Percent Silicate
□ μ eo @ .2%
● μ eo @ .4%
■ μ eo @ .6%

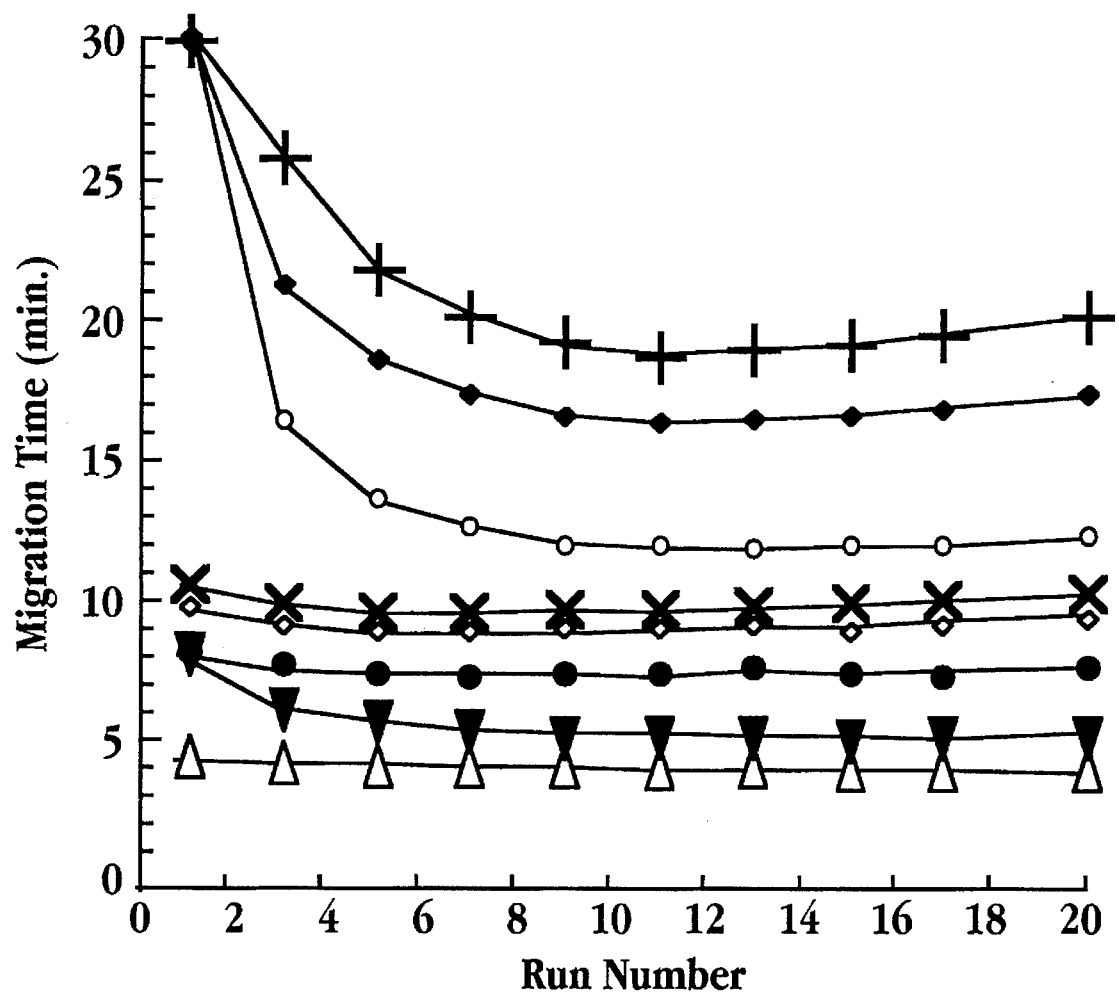
Fig. 7
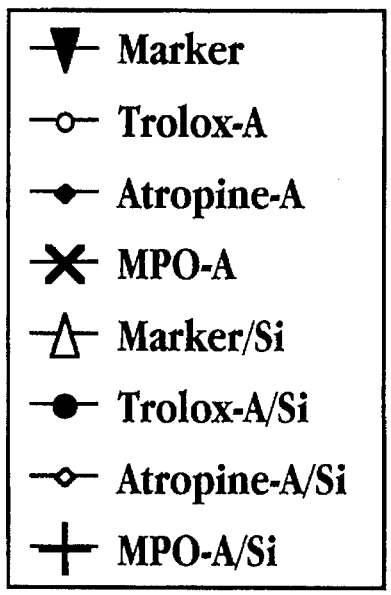

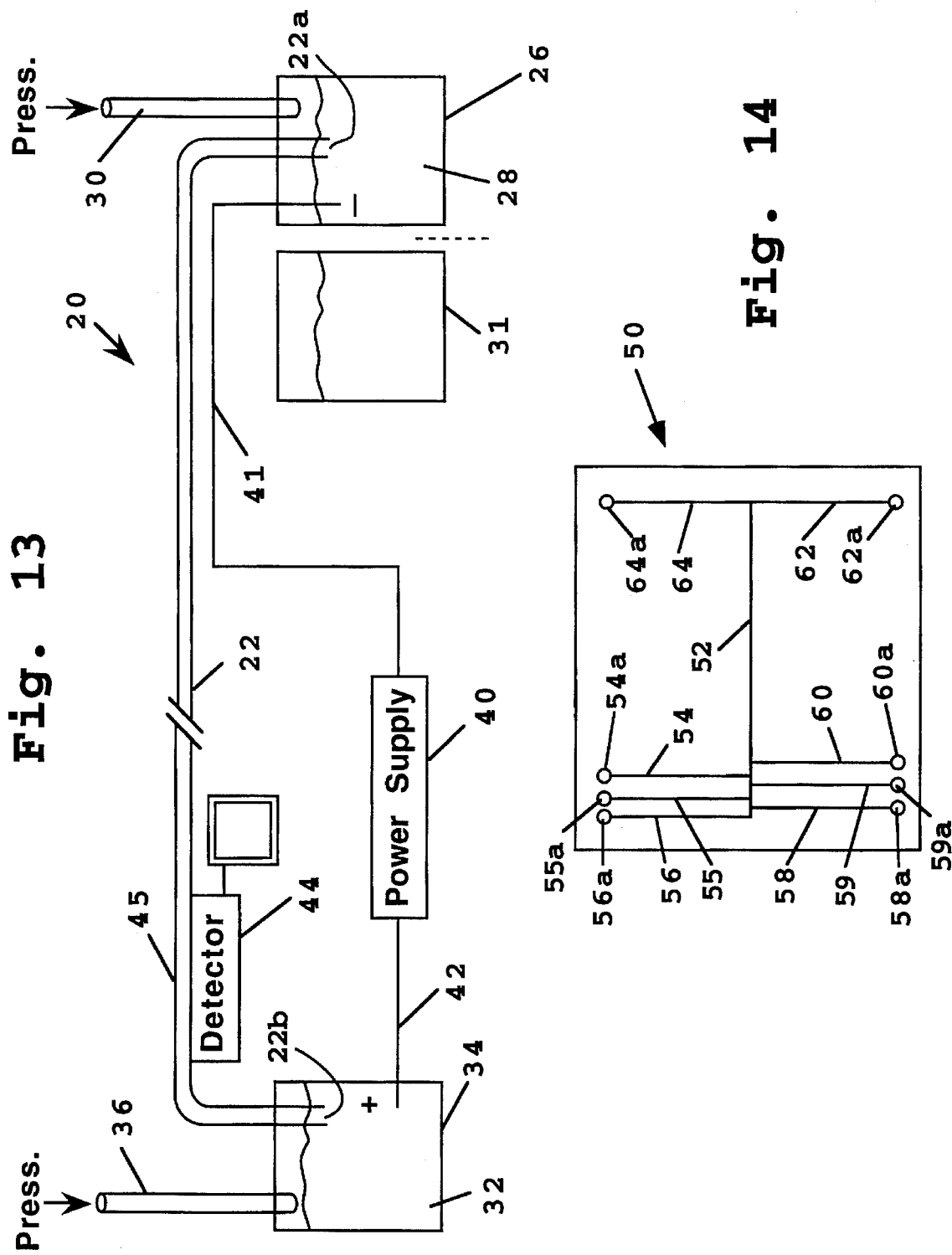

METHOD AND SILICATE COMPOSITION FOR CONDITIONING SILICA SURFACES

FIELD OF THE INVENTION

The present invention relates to a method and composition for conditioning a silica surface for use in separating chemical and biochemical analytes.

REFERENCES

Anderson, D. J., *Anal. Chem.* 67:475R (1995).

Atamna, K. D., et al., *J. Liq. Chrom.* 13:2517–2528 (1990).

Boom, R., et al., *J. Clin. Microbiol.* 28:495–503 (1990).

Falcone, J. S., et al., "Silicates" in *Encyclopedia of Polymer Science and Engineering*, Vol. 15, 2nd Edition, Wiley Publishing, NY, pp. 178–204 (1985).

Grob, K., *Making and Manipulating Capillary Columns for Gas Chromatography*, Alfred Huthig Verlag, New York, N.Y.(1986).

Grossman, P. D., and Colburn, J. C., Eds., *Capillary Electrophoresis*, Academic Press, Inc., San Diego, Calif. (1992).

Hearn, M. T. W., Ed., *HPLC of Proteins, Peptides, and Polynucleotides*, VCH, New York, N.Y. (1991).

Henry, M. P., *J. Chrom.* 544:413 (1991).

Jacobson, S. C., et al., *Anal. Chem.* 66:4127–4132 (1994a).

Jacobson, S. C., et al., *Anal. Chem.* 66:1107–1113 (1994b)

Majors, R. E., *LC.GC* 12:203 (1994).

Manz, A., et al. *J. Micromech. Microeng.* 4:257–265 (1994a).

McCormick, R., *Anal. Chem.* 60:2322–2328 (1988).

Otsuka, K., *J. Microcol. Sep.* 1:150–154 (1989).

Snyder, L. R., and Kirkland J. J., *Introduction to Modern Liquid Chromatography*, 2nd Ed., John Wiley & Sons, Incl, New York, N.Y. (1979).

Unger, K. K., Ed., *Packings and Stationary Phases in Chromatographic Techniques*, Marcel Dekker, New York, N.Y. (1990).

Unger, K. K., and Trudinger, U., Chap. 3 in *High Performance Liquid Chromatography*, Brown, P. R. and Hartwick, R. A., Eds, John Wiley, New York, N.Y. (1989).

Vogelstein, B., et al., *Proc. Natl. Acad. Sci. USA* 76:615–619 (1979).

Wiktorowicz, J. E., and Colburn, J. D., *Electrophoresis* 1990 11:769–773 (1990).

Wiktorowicz, J. E., U.S. Pat. No. 5,015,350 (1991).

Yang, R. C. A., et al., *Meth. Enzymol.* 65:176–182 (1979).

BACKGROUND OF THE INVENTION

Silica surfaces play an important role in the purification and analysis of chemical and biochemical analytes. In chromatographic applications, silica matrices (e.g., comprising beads or gels) have been used for decades to separate organic compounds based on differences in binding affinities under selected solvent conditions. In recent years, applications of silica matrices have been expanded to include separating non-traditional materials, such as nucleic acids, for example.

Silica gels and beads have also been used as solid-phase supports for attaching, covalently or by adsorption, coating materials that impart unique and highly advantageous separation properties. For example, a vast number of derivatized silica gel materials have been developed for analytical and preparative standard and high-pressure liquid chromatography (HPLC) to provide high-resolution separations.

Silica surfaces have also been used in the form of glass plates, tubes, and channels, to define passageways in which sample materials migrate during chromatographic or electrophoretic separations. In many of these applications, including uses in chromatography, slab gel electrophoresis, and capillary electrophoresis, it is often desired that the silica surface be inert towards the analytes of interest so as not to interfere with the separation process. For example, glass plates and columns have been treated with blocking agents, such as dichlorodimethylsilane and other silylating agents, to block surface silanol groups which would otherwise adsorb analytes or interfere with the separation medium.

In electrophoretic techiques carried out in silica-lined channels, particularly with narrow channels, the physical condition of the silica surface can have a significant effect on analyte mobility as a consequence of electroosmotic flow. Electroosmotic flow (EOF) is the bulk flow of the liquid electrophoresis medium which arises due to the effect of the electric field on counterions adjacent to the negatively charged channel wall. Because the channel wall is negatively charged under most pH conditions, there is a build-up of positive counterions (cations) in the solution adjacent to the wall. In an electric field, this cylindrical shell of cations causes the bulk flow of the medium to assume the character of a positively charged column of fluid which migrates toward the cathodic electrode at an EOF rate dependent on the thickness of the shell.

The rate of EOF can provide an important variable that can be optimized to improve the separation of two or more closely migrating species. In particular, when electrophoresis is carried out under conditions in which EOF and the migration of species to be separated are in opposite directions, the effective column length for separation can be made extemely long by making the rate of EOF in one direction nearly equal to the electrophoretic migration rate of the analyte attracted most strongly in the opposite direction by the electric field. A significant problem with using such conditions in capillary electrophoresis (CE) applications has been that the rate of EOF is highly sensitive to the nature and composition of the selected electrophoretic medium, as well as to the chemical condition of the capillary wall. That is, it has been difficult to sustain consistent migration times from run to run and from capillary to capillary due to chemical changes at the surface of the capillary wall after successive runs, and due to variability in the condition of the capillary walls of different capillary tubes from the same or different suppliers.

SUMMARY OF THE INVENTION

The invention includes, in one aspect, a method for increasing the electroosmotic flow rate available for a silica surface. In the method, there is provided an electrophoretic channel which is defined by one or more silica surfaces. The surface(s) are contacted with an alkaline aqueous solution containing a solubilized silicate-monovalent metal complex in an amount effective to increase the acidity of the silica surface(s), as evidenced by a reduction in the average bulk pKa of the surface(s). The achieved increase in acidity is greater than would be obtained using an otherwise identical solution lacking said silicate. In one preferred embodiment, the monovalent metal used in the solution is $Li^+$, $Na^+$, or $K^+$. Prior to treatment with silicate reagent, the silica surface(s) may be contacted with an aqueous solution of MOH having a pH greater than 11, where M is selected from the group consisting of $Li^+$, $Na^+$, and $K^+$.

In one embodiment, the solution contains a $SiO_2$ concentration which is from 0.05 to 5.0 weight %, preferably from 0.05 to 1.0 weight %. In yet a more preferred embodiment, the concentration is from 0.2 to 0.5 weight %.

One advantage of the method is that the maximum possible electroosmotic flow of the capillary tube is increased, allowing improved separations of analytes of interest. The method is especially useful in association with counter-current separation methods, such as micellar electrokinetic capillary chromatography (MECC).

In a related aspect, the invention includes an electrophoresis method for analysis of one or more sample analytes. In the method, there is provided a silica surface which defines an electrophoretic channel having an inlet end and an outlet end. The surface is contacted with a silicate solution of the type above, in an amount effective to increase the acidity of the silica surface. After a selected time, the alkaline aqueous solution is replaced with running buffer, and the sample is loaded into the inlet end of the channel. The ends of the channel are immersed in anodic and cathodic reservoirs containing electrolyte solution, and an electric field is applied across the ends of the channel under conditions effective to induce the analyte(s) to migrate toward the outlet end of the tube for detection.

In a more general aspect, the invention includes a method for increasing the acidity of a silica surface, by contacting the surface with an alkaline aqueous solution of the type above, in an amount effective to increase the acidity of the silica surface(s), as evidenced by a reduction in the average bulk pKa of the surface(s). Again, the achieved increase in acidity is greater than would be obtained using an otherwise identical solution lacking said silicate. The method can be used to enhance the physical properties of a variety of silica surfaces, including those of capillary tubes, microchannels formed on microchips, glass plates, silica beads used in liquid chromatography, and capillary surfaces used in gas chromatography. Prior to treatment with silicate reagent, the silica surface(s) may be contacted with an aqueous solution of MOH having a pH greater than 11, where M is selected from the group consisting of $Li^+$, $Na^+$, and $K^+$.

In one embodiment, the method is useful for preparing a silica surface which is to be subsequently derivatized with a covalently or non-covalently attached chemical coating. In the method, an underivatized silica surface is contacted with an alkaline aqueous silicate solution of the type above, in an amount effective to increase the acidity of the silica surface. After the alkaline solution is removed, the surface is contacted with a derivating agent under conditions effective to allow the derivatizing agent to bind to the surface. In a preferred embodiment, the derivatizing agent is covalently bound to the silica surface.

The invention also includes fused silica capillary tubes, microchannel-containing microchips, and silica beads produced using the silicate solution.

In another aspect, the invention includes an improvement in a method for capturing a nucleic acid on a silica particle. The improvement resides in the step of, prior to nucleic acid capture, contacting the silica particle with an alkaline aqueous solution containing a soluble silicate-monovalent metal complex in an amount effective to increase the acidity of the silica particle, whereby the binding capacity of the silica particle for the nucleic acid is increased. In one embodiment, the silica particle may be contacted with an aqueous solution of MOH of the type above, prior to contact of the particle with silicate solution.

Also included are kits for use in carrying out the methods above. The kits include a silicate reagent solution of the type described herein, together with other reagents as appropriate for the selected application. In one embodiment, for capillary electrophoresis applications, a kit will include a stock solution of silicate reagent in a carbon dioxide impermeable container, and selected buffer reagents and additives appropriate for electrophoretic sepration.

These and other objects and features of the invention will become more fully apparent when the following detailed description of the invention is read in conjunction with the accompanying drawings.

BRIEF DESCRIPTION OF THE DRAWINGS

FIG. 7 shows a plot of EOF mobilities obtained for 20 consecutive electrophoretic separations of a neutral marker and three charged standards in 20 mM sodium acetate running buffer, pH 4.5, where the capillary tube had been preconditioned either with NaOH solution alone or with a silicate/NaOH mixture (0.2% $SiO_2$/100 mM NaOH, designated by "/Si" in legend);

Figure 10:
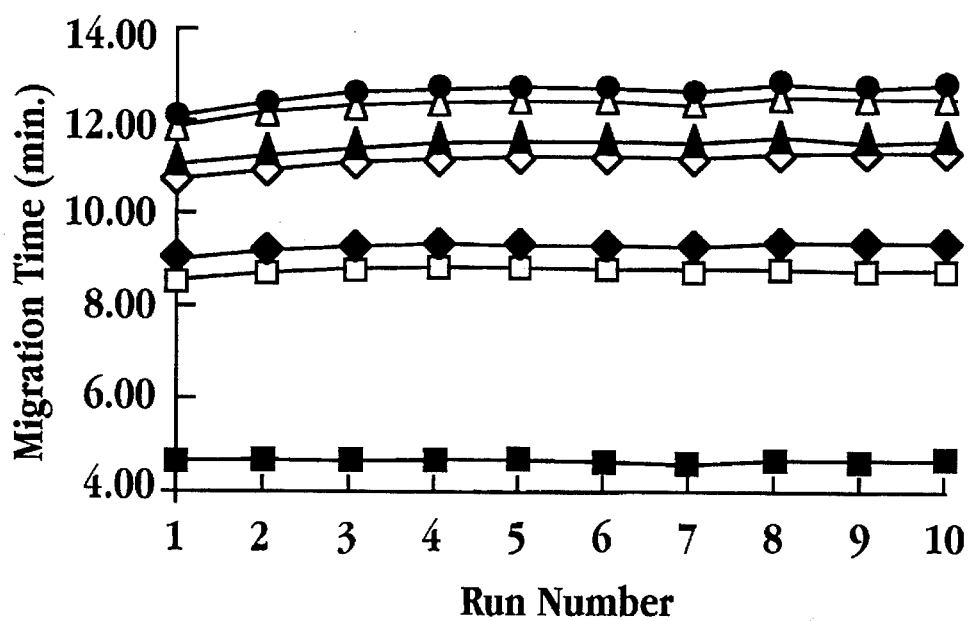
Figure 9A:
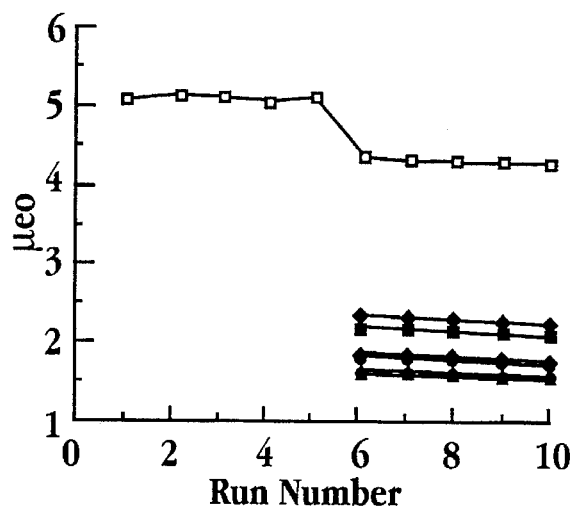
Figure 9B:
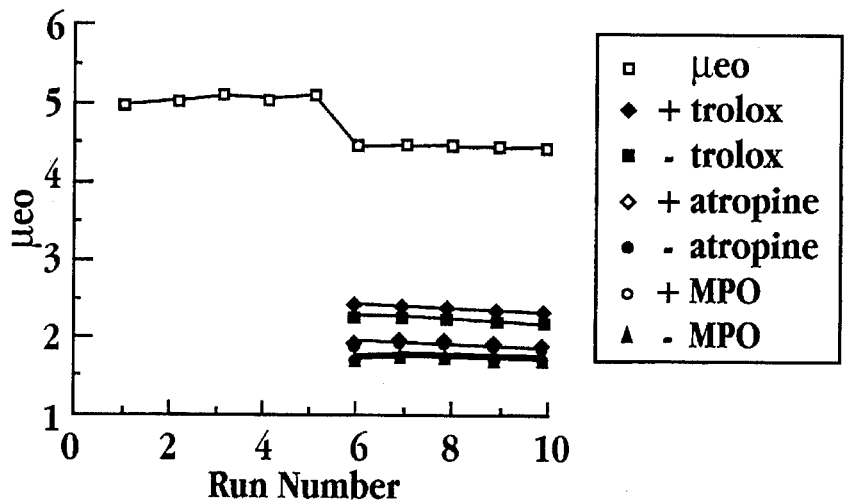
Figure 9C:
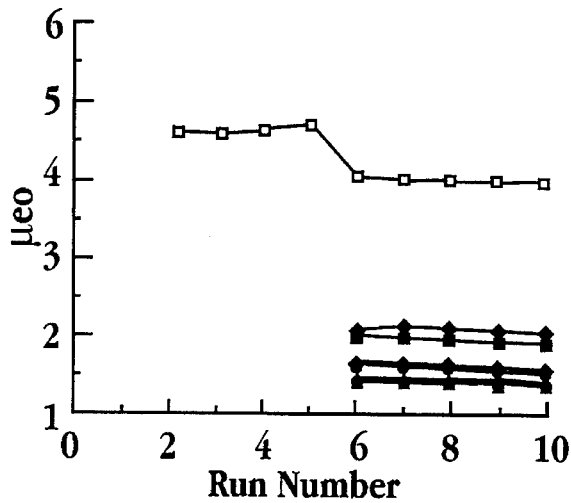
Figure 9D:
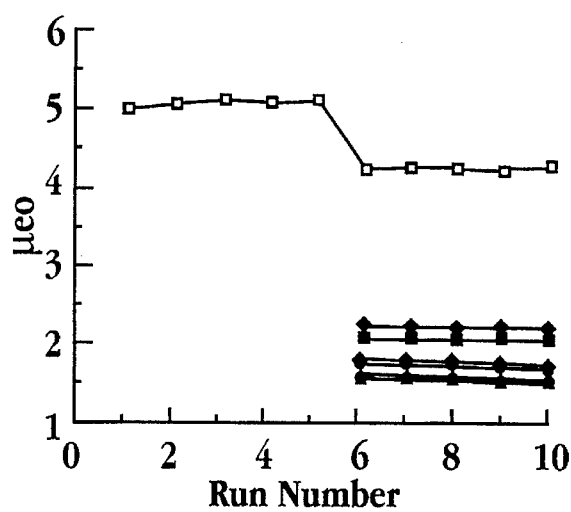
Figure 9E:
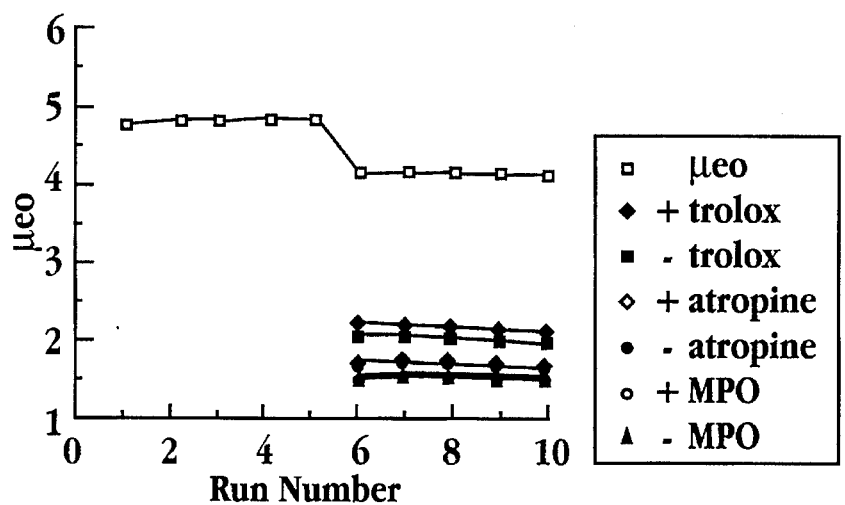
Figure 9F:
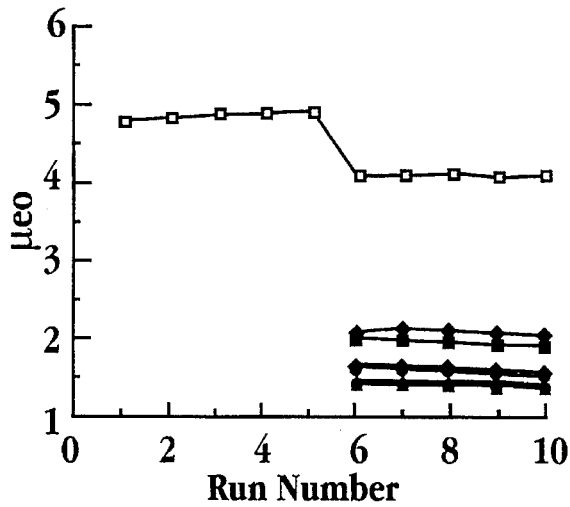
Figure 11A:
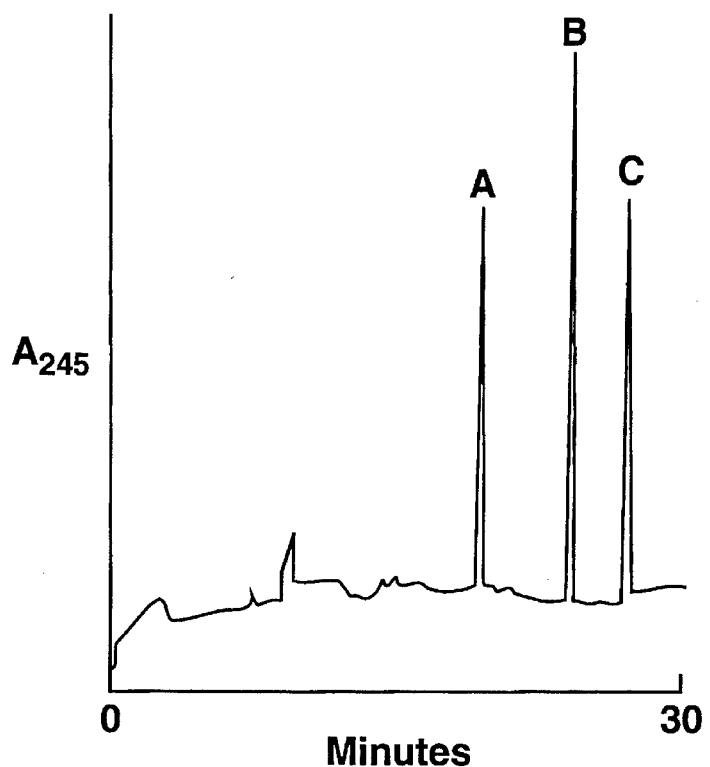
Figure 11B:
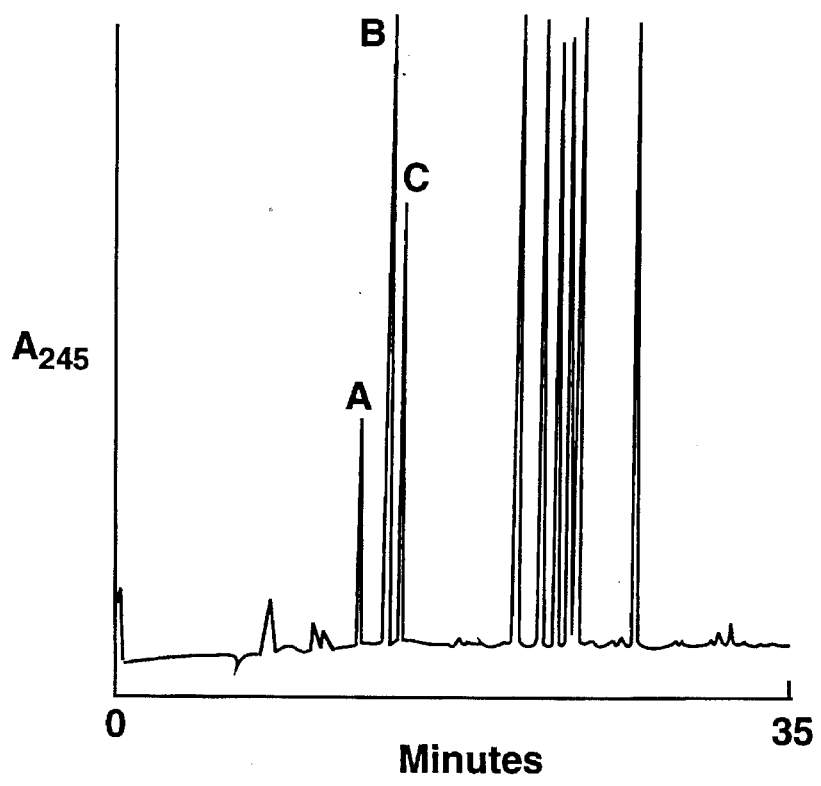
Figure 12:
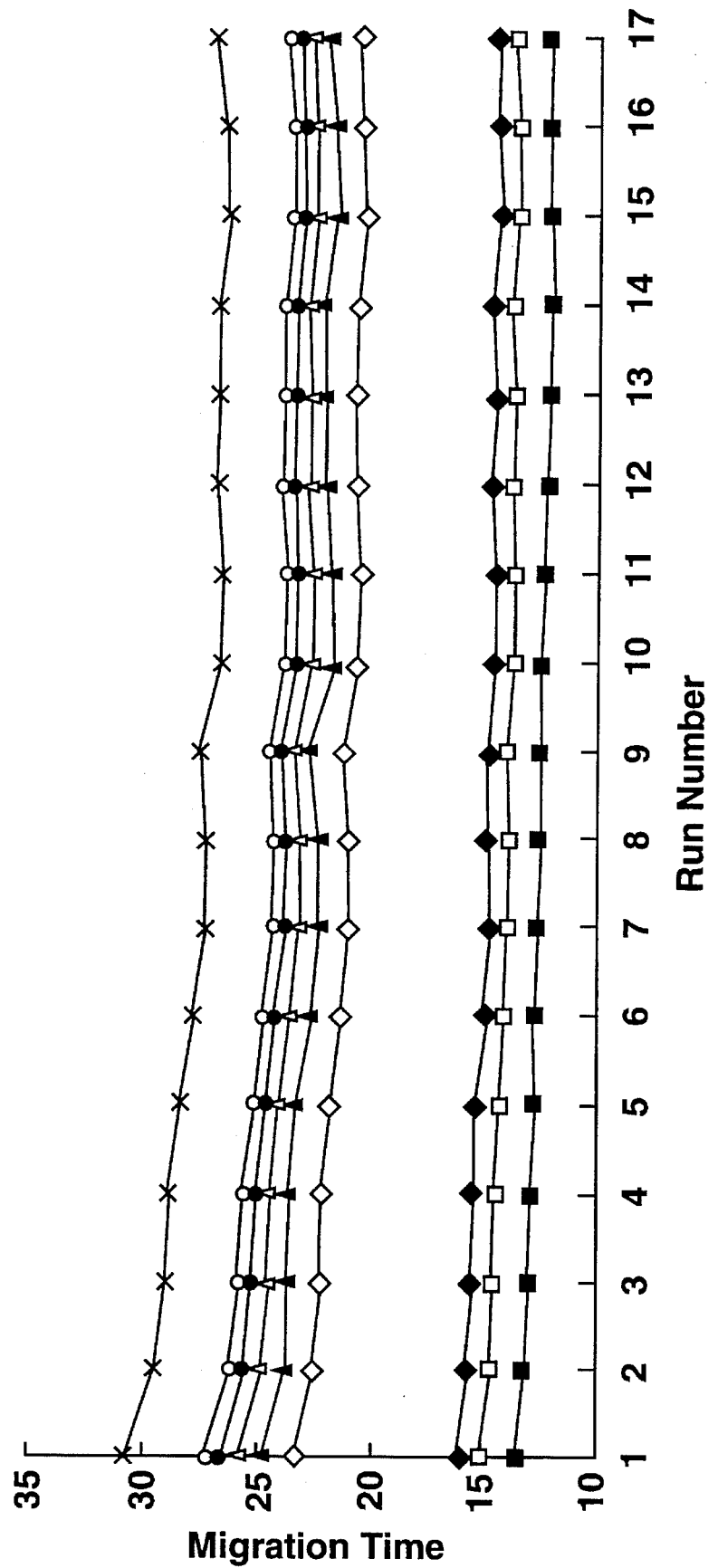

SiO$_2$ (lowest to highest curve), the latter two curves differing in the time of exposure to silicate reagent (Example 7);

FIGS. 9A–9F shows plots of EOF mobility and electrophoretic mobilities obtained with DMSO and a mixture of 3 chiral compounds, as obtained with otherwise identical capillary tubes obtained from 6 different suppliers, where the capillary tube was washed with 0.25% SiO$_2$/100 mM NaOH prior to each run;

FIG. 10 shows a plot of EOF mobilities for DMSO and the chiral mixture used in FIGS. 9A–9F, as measured in 10 consecutive runs under the same conditions;

FIGS. 11A–11B shows electropherograms of a mixture of derivatized monosaccharides separated in a capillary tube which was conditioned first only with NaOH solutions (11A), and in the same capillary tube after pre-conditioning with silicate reagent (0.34% SiO$_2$/100 mM NaOH);

FIG. 12 shows a plot of migration times of the monosaccharide mixture from FIGS. 11A–11B over the course of 17 consecutive runs following exposure of the capillary tube to silicate reagent (0.34% SiO$_2$/100 mM NaOH);

FIG. 13 shows a schematic view of a capillary electrophoresis system which may be used in practicing the invention; and FIG. 14 shows a schematic view of a miniature capillary electrophoresis system formed in a microchip.

DETAILED DESCRIPTION OF THE INVENTION

The present invention provides, in its broadest embodiment, a method for increasing the acidity of a silica surface by contacting the surface with an alkaline aqueous silicate solution of the type detailed below. In one aspect, the method is used to increase the maximum possible electroosmotic flow (EOF) of electrophoretic channel defined by one or more silica surfaces. This feature is especially useful in countercurrent electrophoresis formats. In a second aspect, the method can be used to increase the acidity of a silica surface, as a means of activating the surface for derivatization with a coating agent. In this aspect, the method can be used to prepare derivatized silica surfaces for electrophoresis, as well as derivatized solid supports for chromatographic applications such as liquid chromatography and gas chromatography.

As used herein, the term "silica" refers to a solid material consisting predominantly of SiO$_2$ and/or silicic acid groups (H$_2$SiO$_3$).

"Silica surface" refers to a surface consisting predominantly or entirely of SiO$_2$ and/or silicic acid groups. The term as used herein encompass such surfaces present on pure forms of SiO$_2$ (such as quartz, cristobalits, or fused silica), as wells as those of silicate glasses.

"Soluble silicate" or "soluble silicate-monovalent metal complex" refers to a silicate composition of the general formula M$_2$O·(SiO$_2$)$_m$·(H$_2$O)$_n$, where m and n are integers and M is an alkali metal, i.e., lithium, sodium, potassium, rubidium, cesium, or francium, most commonly lithium (Li), sodium (Na), or potassium (K). The term encompasses all soluble monomeric, linear, branched, and cyclic silicate structures in equilibrium in an alkaline aqueous solution.

"Alkaline" as used herein, refers to a solution having a pH$\geq$10.

I. Silicate Reagent

The soluble silicate reagent of the invention is generally an alkaline aqueous solution containing a soluble silicate in an amount effective to reduce the average bulk pKa of the silica surface. The soluble silicate has the general formula M$_2$O·(SiO$_2$)$_m$·(H$_2$O)$_n$, where m and n are integers and M is an alkali metal, most usually lithium, sodium, potassium, or a mixture thereof. The silicates form a number of structures in alkaline solution, including orthosilicate (SiO$_4^{4-}$), pyrosilicate (Si$_2$O$_7^{6-}$) and longer linear structures, and cyclic and branched structures, all of which are in dynamic equilibrium under alkaline conditions, particularly with pH$\geq$10. The distribution among possible structures depends on several factors including the concentration of SiO$_2$, the ratio of SiO$_2$ to alkali metal, and temperature.

The silicate reagent is prepared by any suitable means known in the art. Suitable solutions may be prepared by solubilization of crystalline, powdered, or glass-state SiO$_2$ in aqueous LiOH, NaOH, or KOH, for example, optionally under elevated temperature and pressure to accelerate dissolution. Alternatively, silicate salts in dry form, such as Na$_2$SiO$_3$, Na$_6$Si$_2$O$_7$, Na$_2$Si$_3$O$_7$, K$_2$Si$_2$O$_5$, K$_2$Si$_3$O$_7$, and Li$_2$SiO$_3$, may be dissolved in water or aqueous hydroxide to prepare a solution of desired concentration. The concentration of alkali metal M may be adjusted by suitable titration using concentrated LiOH, NaOH, or KOH, as appropriate. Silicate stock solutions are also available from commercial suppliers. For example, aqueous lithium silicate (Li$_2$SiO$_3$, 20 weight %) is available from Aldrich Chem. Co. (Milwaukee, Wisc.), and sodium silicate (27% SiO$_2$/14% NaOH) is available from Aldrich and Fluka (Ronkonkoma, N.Y.). The pH of the silicate reagent of the invention is usually greater than 10, preferably greater than 11, and more preferably greater than 12. Most commonly, the monovalent metal is sodium.

It will be appreciated that, given the high concentration of hydroxide ion in the silicate reagent, the reagent readily captures carbon dioxide (CO$_2$) from the surrounding atmosphere, forming carbonate ions in the reagent. Although the presence of carbonate ions in the reagent can be tolerated to some degree without significantly diminishing the reagent's advantageous effects, exposure to carbon dioxide should be avoided. To minimize carbonate formation, the reagent should be kept in a sealed container, preferably in an inert atmosphere (e.g., argon or nitrogen). Further advantages in this regard may be achieved by preparing the silicate reagent in a glove-box, dry-box, or other suitably controlled atmosphere which is substantially devoid of water vapor and CO$_2$.

In a preferred embodiment, the silicate reagent is prepared as a concentrated stock solution in one or more sealable containers containing a selected amount of reagent, e.g., a volume sufficient for one-day or one-month use. For example, a 10× silicate stock consisting of ~3% SiO$_2$ in 1N NaOH (for preparing working solutions containing 0.3% SiO$_2$ in 0.1N NaOH can be used for a month or more when stored in an air-tight container between uses. Working solutions are prepared daily by dilution of concentrated silicate stock with water, preferably in plastic tubes.

The container is generally made of any CO$_2$-impermeable material which is chemically inert with respect to the silicate reagent. Glass containers should be avoided since the high alkalinity of the silicate reagent can cause leaching of variable amounts of silicates from the glass surface and into the stock solution. Suitable container materials include polypropylene, polyethylene, "TEFLON" and the like The container may additionally include a septum to allow removal of aliquots of the reagent by syringe. For long-term storage or transport, the vial is preferably placed in a sealed bag (e.g., a polyethylene bag) flushed with argon gas. In studies conducted in support of the invention, the applicants have found that silicate reagent solutions in accordance with the invention remain stable (i.e., retain full efficacy) for at least two months when packaged in a polypropylene container sealed in a polyethylene bag under argon atmosphere.

II. Applications in Electrophoresis

In one aspect, the invention includes a method for increasing the acidity of a silica surface, by contacting the surface with an alkaline aqueous solution of the type above, in an amount effective to increase the acidity of the silica surfaces. As applied to electrophoretic applications, the method encompasses several related embodiments. First, the method can be used to increase endoosmotic flow of an underivatized silica surface, by increasing the number of negatively charged silanol groups along the surface. Second, the method can be used to expand the pH range over which high EOF can be obtained, by reducing the average bulk pKa of the silica surface. Third, by increasing the number of silanol groups on the silica surface, the method can be used to enhance the reactivity of the surface towards coating agents used to reduce or reverse EOF, to reduce interactions with analytes and medium components, or to anchor a cross-linked separation matrix to the silica surface.

As will be seen further below, the method provides a number of significant improvements over prior art methods. When used to increase EOF, the method provides rate enhancements and overall run-to-run consistency better than previously available using non-silicate alkaline solutions such as 0.1 to 1N NaOH. When the silicate reagent of the invention is used periodically between successive runs, the method is effective to maintain EOF at consistent levels over many electrophoretic runs, simplifying the analyses of comparative samples. Furthermore, the silicate reagent can be used to regenerate the condition of the silica surface after exposure to harsh conditions (e.g., acidic pH), extending the useful lifetime of the surface for electrophoresis. When used as a preliminary step for derivatization with a coating, the method can be used to control the density and uniformity of coating, improving batch-to-batch reproducibility of such coatings and the coating's durability.

A. Electrophoresis System

General considerations regarding electrophoresis protocols are illustrated in this section using capillary tube electrophoresis as an example. However, it will be recognized that the discussion is also applicable to other narrow channel formats, such as capillary electrophoresis performed in a micro-channel formed in the glass or silica substrate of a microchip.

FIG. 13 shows a simplified schematic view of a capillary electrophoresis system 20 (Applied Biosystems, Foster City Calif.) suitable for practicing the method of the invention. The system includes a capillary tube 22 having a length preferably between about 10–200 cm, typically less than about 100 cm, and an inner diameter (i.d.) of preferably between about 10–200 μm (microns), typically about 50 μm. Capillary tubes with rectangular or square cross-sections are also contemplated. One preferred capillary tube is a fused silica tube having an inner diameter of 50 μm (available from Polymicro Technologies, Phoenix, Ariz.).

More generally, the capillary tube may be any channel capable of supporting a column of electrolyte solution, preferably having an inner diameter of 200 μm or less.

A cathodic reservoir 26 in system 20 contains an electrolyte solution 28. The cathodic end of the tube, indicated at 22a, is sealed within reservoir 26 and is immersed in electrolyte solution, as shown, during electrophoresis. Second tube 30 in reservoir 26 is connected to a finely controlled air pressure system (not shown) which can be used to control the pressure in the head space above the solution, e.g., for loading electrolyte solution into the tube by positive pressure. The pressure system is able to generate a pressure differential across the ends of the capillary tube of about 100–300 psi or less. Alternatively or in addition, the air pressure system can include a vacuum system for drawing solution through the capillary tube.

A sample reservoir 31 in system 20 contains the sample mixture to be loaded into the inlet end of the tube (assumed here to be the cathodic end). The sample and cathodic reservoirs may be carried on a carousel or the like, for placement at a position in which the cathodic end of the tube can be immersed in the reservoir fluid. Although not shown here, the carousel may carry additional reservoirs containing, for example, solutions for cleaning and flushing the tube between electrophoretic runs, or different electrophoretic media.

The opposite end of the tube (assumed here to be the anodic end), indicated at 22b, is immersed in an anodic electrolyte solution 32 contained in an anodic reservoir 34. A second tube 36 in reservoir 34, analogous to tube 30 in reservoir 26, can be included to control the pressure above solution 32, e.g., for loading solution into the tube, just as with tube 30 in reservoir 26. Typically, the compositions of electrolyte solutions 28 and 32 are identical. However, in certain applications, particularly isotachophoresis, the electrolyte solutions at each end may be different.

For sample loading and subsequent sample separation by electrophoresis, the filled capillary tube and electrode reservoirs are preferably configured so that there is little or no net hydrodynamic flow through the tube. This can be effected by keeping the surfaces of the electrode reservoir solutions at the same height, or by controlling the atmospheric pressures above the two solutions.

A high voltage supply 40 in the system is connected to the cathodic and anodic reservoirs as shown, for applying a selected electric potential between the two reservoirs. The power supply leads are connected to platinum electrodes 41, 42 in the cathodic and anodic reservoirs, respectively. The power supply may be designed for applying a constant voltage (DC) across the electrodes, preferably at a voltage setting of between 6 kV and 30 kV.

Detector 44 in the system is positioned adjacent the anodic end of the tube, for monitoring sample peaks migrating through an optical detection zone 45 in the tube. Typically, the capillary tubing has been treated to remove a small region of exterior polyimide coating (in the case of a polyimide-coated capillary tube) to create a small window. The detector may be designed for any mode of detection known in the art, including UV/visible absorption detection, conductivity detection, fluorescence emission detection, radioisotope detection, and mass-spectrometric detection, for example.

In operation, the capillary tube is washed by flushing suitable rinsing solutions through the tube by applying positive or negative pressure to the head space above the appropriate solution reservoir. Alternatively, the capillary can be washed manually by syringe. If a cleaning solution different from the electrolyte solution (running buffer) is used, the tube is finally flushed with several volumes of running buffer before use.

The sample is then loaded into the inlet end of the tube, typically by electrokinetic injection for charged species, and by hydrostatic injection for neutral species. After sample loading, the tube end is returned to the solution in cathodic reservoir 26, and a separation voltage (e.g., 30 kV) is applied until the desired number of fragment peaks have passed through the detection zone.

For automated electrophoresis of multiple samples, the apparatus may be adapted to include an array of capillary tubes and suitable detection means for simultaneous monitoring of sample migration in the tubes. By such an arrangement, the same sample or a number of different samples can be analyzed in parallel using such an array.

B. Improved Surface Properties

The composition of the silicate reagent for a particular application may be optimized for the particular analyte separation to be carried out, on the basis of test studies over a range of silicate and monovalent metal concentrations as illustrated below.

Figure 1:
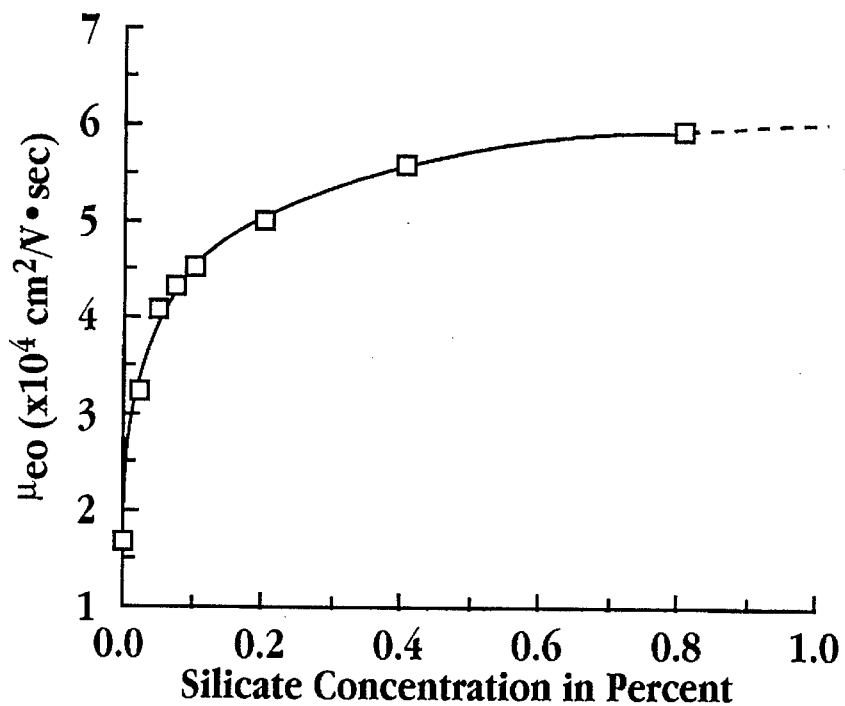
FIG. 1 shows a plot of EOF mobility values ($\mu_{EO}$) measured by capillary electrophoresis (CE) of DMSO in 20 mM sodium acetate buffer, pH 4.5, as a function of concentration of silicate reagent (0.03 to 0.8% $SiO_2$/100 mM NaOH) used in conditioning and pre-run cycles.

FIG. 1 shows a general trend of EOF mobilities achieved following conditioning of a fused silica capillary tube with silicate reagent as a function of concentrations of $SiO_2$. As can be seen, the measured mobilities generally increases as a function of silicate concentration with maximal EOF being reached at about 0.4 wt % $SiO_2$. Details of this study are given in Example 1.

As discussed above, the silicate reagent of the invention may be prepared from a number of silicate sources. Because of the relatively high alkalinity of the silicate reagent, the reagent contains a number of silicate structures in rapid equilibrium, independent of the initial structures in the silicate source. The steady-state distribution of species is dependent on several factors, including total concentration of $SiO_2$, concentration of hydroxide ion, and the identity of the alkali metal.

Figure 2:
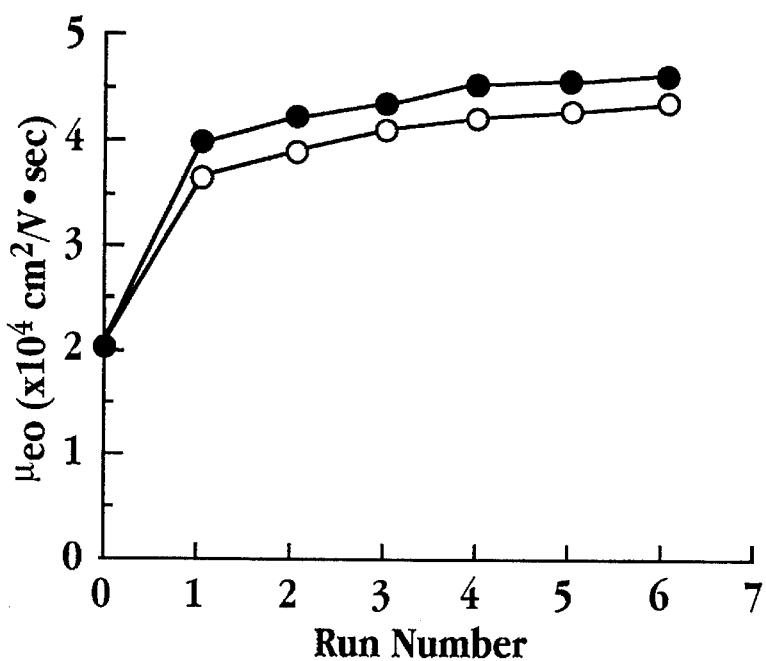
FIG. 2 shows a plot of EOF mobilities obtained using silicate reagent solutions formed from a sodium silicate stock solution (27% $SiO_2$/14% NaOH) (upper curve) and a solution prepared from solid anhydrous sodium metasilicate (lower curve)

The flexibility in terms of silicate source material is illustrated in FIG. 2, which shows EOF mobilities measured in 6 successive electrophoresis runs following pre-conditioning of capillary tubes with either of two silicate reagent solutions containing 0.25% $SiO_2$/100 mM NaOH (Example 2). One of the reagent solutions was prepared from a commercial stock solution of sodium silicate (27% $SiO_2$/14% NaOH). The other was prepared from an aqueous stock solution made from anhydrous sodium metasilicate powder ($Na_2SiO_3$). As can be seen from FIG. 2, the two reagent solutions provide substantially the same EOF profiles. These results indicate that performance of the silicate reagent is independent of whether the source is a commercial alkaline stock solution or a polymeric silicate solid.

Figure 3:
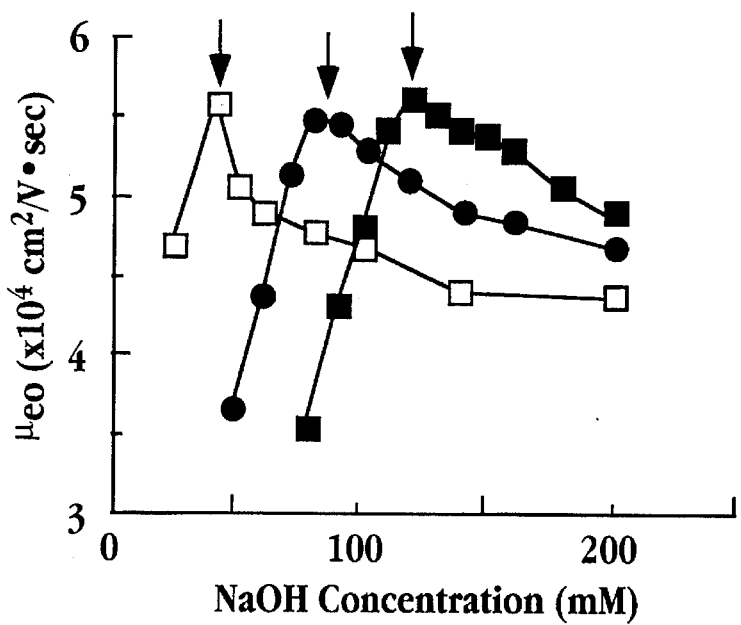
FIG. 3 shows a plot of three EOF mobility curves obtained in a conditioning study with three different silicate concentrations over several NaOH concentrations (~25–200 mM NaOH): left-hand curve, 0.2% $SiO_2$; middle curve, 0.4% $SiO_2$, right-hand curve, 0.6% $SiO_2$.

FIG. 3 illustrates how reagent performance can depend on the ratio of $SiO_2/Na_2O$. In this study, detailed in Example 3, EOF mobilities were measured following capillary treatment with silicate reagent solutions containing 0.2, 0.4, and 0.6 wt % $SiO_2$ concentrations over a range of NaOH concentrations (0.5 to 200 mM). Electrophoresis of neutral marker, DMSO (dimethyl sulfoxide), was conducted in 20 mM sodium acetate, pH 4.5, as with FIGS. 1 and 2. As can be seen from the left-hand curve of FIG. 3, the series of solutions containing 0.2% $SiO_2$ show a maximum EOF ($5.5 \times 10^4$ cm$^2$/V.sec) in the presence of ~37 mM NaOH. The 0.4% and 0.6% $SiO_2$ series show similar EOF maxima at NaOH concentration of about 80 and 120 mM NaOH, respectively. These data indicate that for the $SiO_2$ concentrations tested, maximum EOF mobility is obtained at a $SiO_2/Na_2O$ ratio of about 1.5.

Figure 4A:
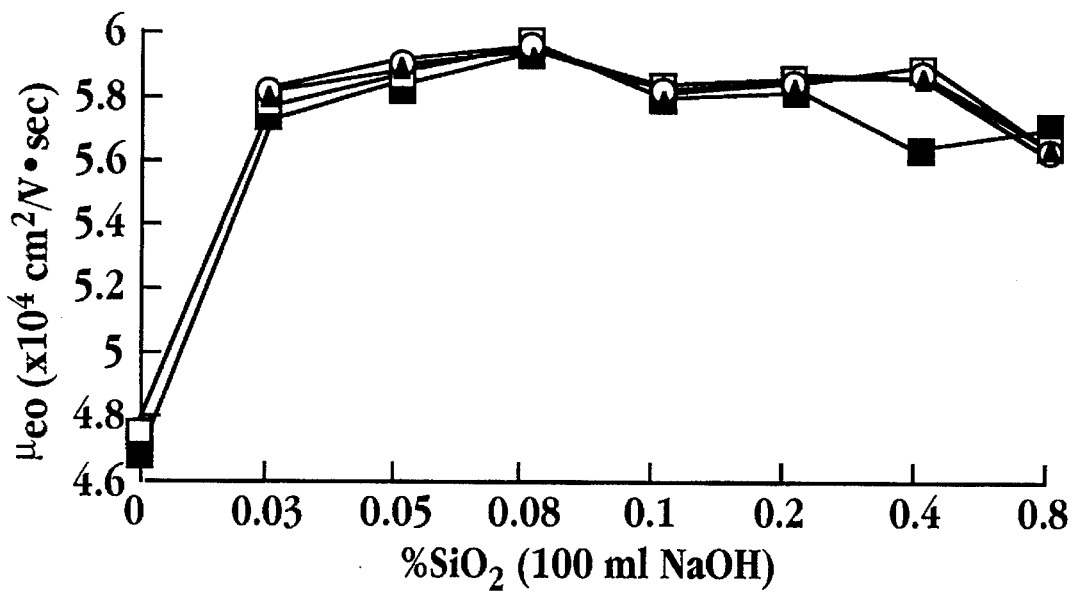
FIGS. 4A–4B show plots of EOF mobilities measured in a Tris/phosphate running buffer, pH 7.4, additionally containing either no SDS (FIG. 4A) or 50 mM SDS (FIG. 4B) following conditioning with silicate reagent containing 100 mM NaOH and $SiO_2$ concentrations ranging from 0 to 0.8% $SiO_2$.

EOF mobilities obtained with a second running buffer (Tris-phosphate, pH 7.4, containing 0, 50 or 100 mM SDS) are shown in FIGS. 4A (0 mM SDS) and 4B (50 mM SDS). As can be seen, EOF mobility is virtually constant over a broad range of $SiO_2$ concentrations (0.03 to 0.8%), regardless of whether SDS is present or absent. It should also be noted that the lower mobilities obtained with the 50 mM SDS buffer (FIG. 4B) are attributable to conductivity-related suppression of EOF due to the presence of the SDS in the buffer.

Figure 5A:
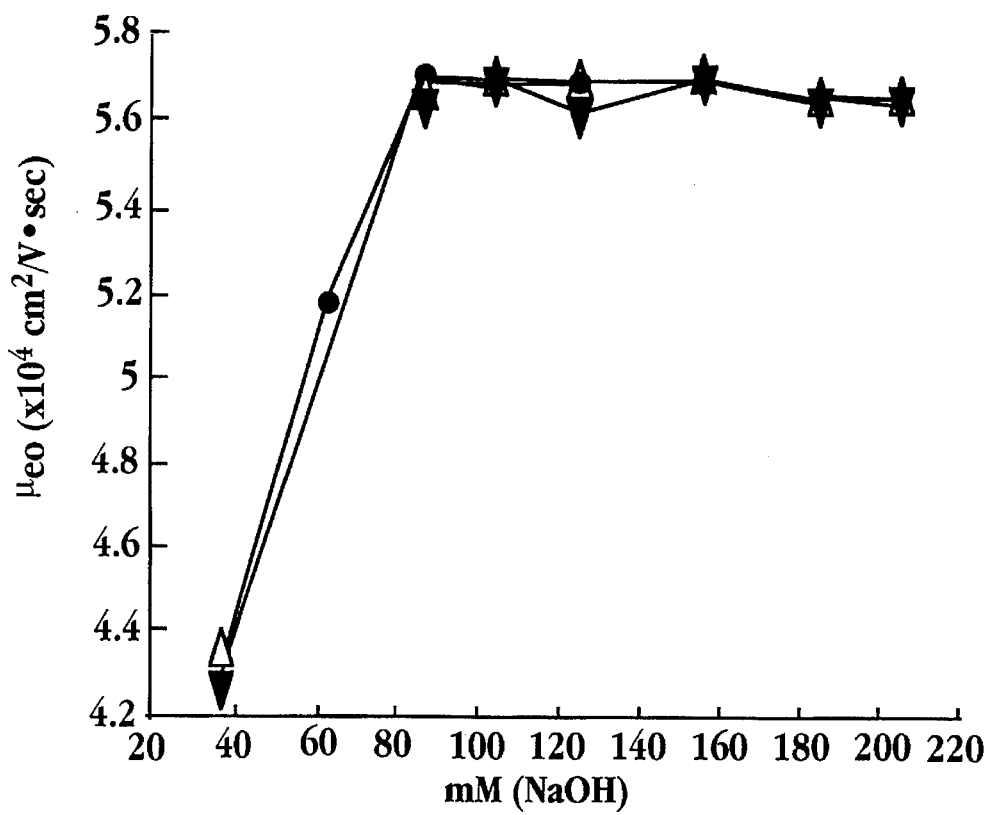
FIGS. 5A–5B show EOF mobility plots obtained under conditions similar to those for FIGS. 4A–4B, except that the silicate concentration for silicate reagent in the pre-run cycles was kept constant at 0.2% $SiO_2$ (5A) or 0.4% $SiO_2$ (5B) while the NaOH concentration was varied (~35–200 mM); the Tris/phosphate running buffer contained 50 mM SDS.
Figure 5B:
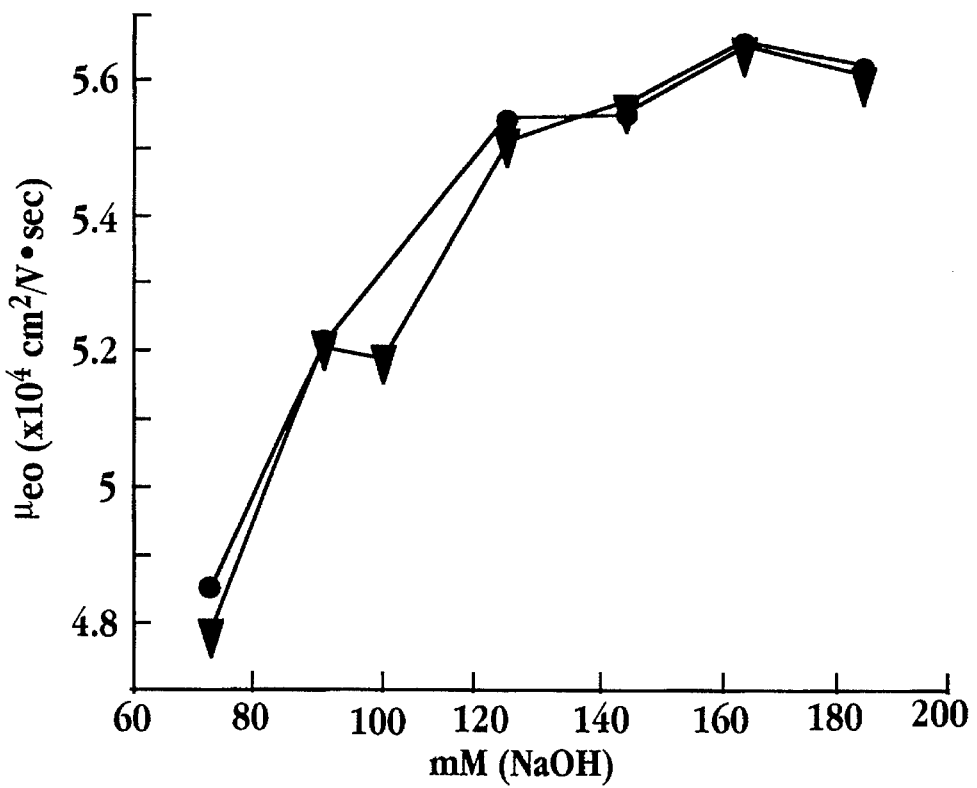

FIGS. 5A and 5B show the mobilities obtained in the Tris-phosphate buffer (containing 50 mM SDS) following capillary conditioning with 0.2 or 0.4% $SiO_2$ over a range of NaOH concentrations. For the 0.2% $SiO_2$ solutions, a maximum mobility of about ($5.7 \times 10^4$ cm$^2$/V.sec) is obtained over a broad range of NaOH concentrations (80 mM NaOH). By way of contrast, maximum EOF with 0.4% $SiO_2$ is not reached until the NaOH concentration had reached about 160 mM. These results indicate that the optimal $SiO_2/Na_2$ ratio, e.g., to obtain maximum EOF, may depend on the separation conditions used.

The effects of varying the exposure time of the silica surface to silicate reagent is illustrated by Example 5. In this study, EOF was measured for five consecutive runs in 20 mM sodium acetate, pH 4.5, after conditioning of the capillary tubes with silicate reagent (0.25% $SiO_2$/100 mM NaOH) for different lengths of time (10, 20, and 30 minutes). As can be seen from FIG. 6, under the conditions tested, the observed mobilities correlate with exposure time, with longer exposure time giving greater mobility. In addition, for the 10 and 20 minute exposures, EOF increases somewhat over the five successive runs, whereas runs following the 30 minute exposure time remain substantially constant.

It will be appreciated how similar studies can be done for other separation conditions to arrive at exposure conditions that afford high and consistent EOF values.

As noted above, the silicate reagent of the invention can be used to achieve greater maximum EOF rates than can be achieved using hydroxide-containing solutions which are silicate-free. This is illustrated in FIG. 7. In this study, detailed in Example 6, a neutral marker (DMSO) and a set of three charged compounds were electrophoretically separated in capillary tubes which had been conditioned with 100 mM NaOH in the presence or absence of soluble silicate (0.2% $SiO_2$). The separation was repeated 20 times in each case, with each run preceded by a pre-cycle wash with 100 mM NaOH or 0.2% $SiO_2$/100 mM NaOH. In the runs performed following conditioning with NaOH solution alone (without silicate), none of the charged compounds eluted within the first 30 minutes for the first run (see FIG. 7). In subsequent runs, the elution times of the charged compounds gradually decreased, reaching relatively steady values after about the ninth run. In contrast, pre-conditioning with silicate reagent afforded rapid migration times for all of the charged compounds even in the first run, with constant levels being reached within the first 5 to 7 runs (FIG. 7). Furthermore, the migration times obtained with silicate reagent were in all cases substantially faster than those obtained where conditioning had been performed with NaOH solution alone. These results clearly demonstrate the superiority of conditioning with the silicate reagent of the invention, compared with conditioning using sodium hydroxide alone.

According to another important feature of the invention, contacting a silica surface, e.g., the inner wall of a capillary tube, with the silicate reagent of the invention is effective to lower the average bulk pKa of the surface, extending the pH range in which EOF can be exploited in electrophoretic separations. As discussed above, EOF is a phenomenon that results from the bulk flow of electrophoretic medium generated by movement of the shell of cations lining the capillary wall towards the cathode. When the pH of the running buffer is substantially greater than the bulk pKa of the capillary wall (e.g., greater than about 1.5 pH units), most of the surface silanol groups are negatively charged by virtue of being deprotonated. However, when the pH is lowered towards the bulk pKa of these groups, a greater proportion of the surface silanol groups become protonated, reducing the number of negatively charged groups on the surface and hence, the size of the cationic shell responsible for EOF. In MECC, for example, the bulk pKa of fused silica has limited the use of non-coated capillary tubes to running conditions having a pH greater than about 6.5. Ideally, for applications where a large EOF is desired, the bulk pKa of the silica surface should be as low as possible to enable good separation over a broader pH range.

Example 7 describes a study in which EOF was measured over a broad pH range following exposure to alkaline solutions containing various concentrations of silicate (0 to 0.3% $SiO_2$). First, a new capillary tube was conditioned with NaOH solution alone, and EOF mobilities were then measured using DMSO marker and buffers having pH values ranging from 11 to 2.5. This procedure was then repeated after preconditioning with increasing concentrations of silicate (0.05, 0.1, and 0.3% $SiO_2$). The 0.3% $SiO_2$ solution was tested twice, with exposure times of 3 and 20 minutes, respectively. The results are shown in FIG. 8.

Figure 8:
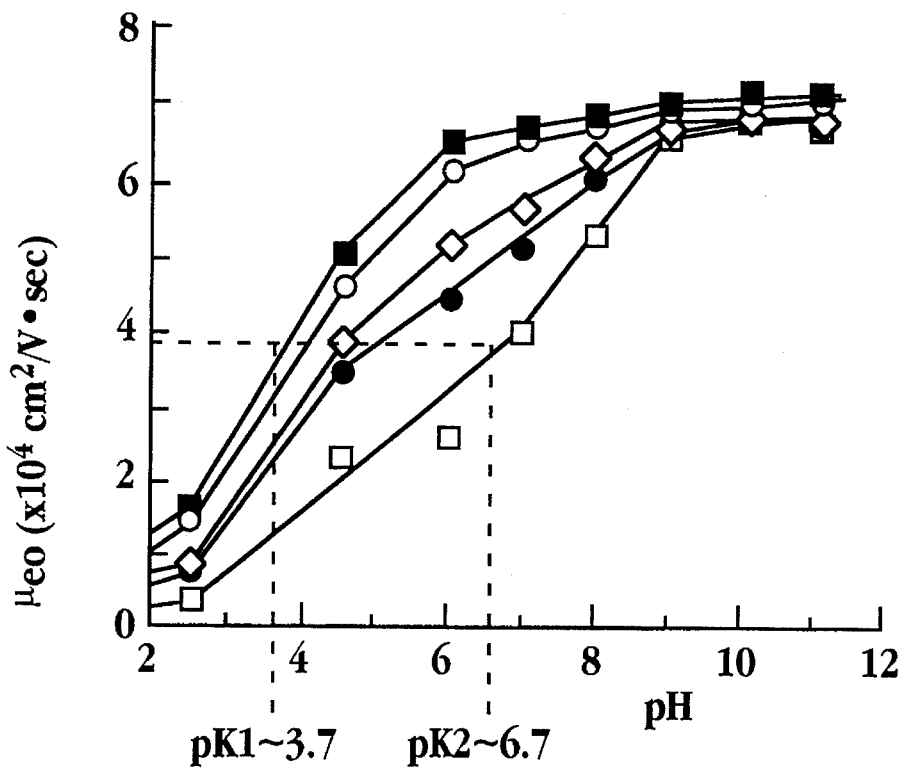
FIG. 8 shows pH profiles of EOF mobilities measured by CE as a function of silicate concentration in the prerun cycle; the silicate concentrations were 0, 0.05, 0.1, 0.3, and 0.3%

With reference to the lowest curve in FIG. 8, preconditioning with NaOH solution alone yields a pH profile in which EOF steadily decreases towards a value of zero at lower pH. The bulk pKa under these conditions is about 6.7, based on the pH at which the EOF is half of maximum. However, upon preconditioning with increasing concentrations of silicate, the bulk pKa of the surface becomes gradually lower. As can be seen, the best results are obtained with the highest silicate concentration tested, for which the bulk pKa is estimated to be about 3.7 (highest curve). The data also show that for the highest silicate concentration, EOF remain at a maximum constant level over a pH range of about 6 to 11, and is still greater than half-maximal at a pH of 4. It is also noted that upon each reconditioning cycle prior to data collection for the next pH profile, the EOF is returned each time to the same EOF maximum (or slightly higher) at pH 11, indicating that use of the silicate reagent delays onset of capillary degradation.

In using the silicate reagent of the invention to increase surface acidity or maximum possible EOF, treatment of the selected silica surface may be preceded by treatment with a concentrated hydroxide solution, preferably with an aqueous solution of MOH having a pH greater than 11, where M is selected from the group consisting of $Li^+$, $Na^+$, and $K^+$. Such pretreatment may be helpful to help activate the surface towards reaction with the silicate reagent, as well as removing impurities and residue from the manufacturing process or from previous electrophoretic runs.

C. Illustrative Applications

The silicate reagent of the invention can be used in association with a variety of capillary electrophoresis techniques, including moving boundary electrophoresis, free zone electrophoresis, electrokinetic capillary chromatography (ECC), isotachophoresis (displacement electrophoresis), and isoelectric focusing.

In one general embodiment, the silicate reagent is used to increase maximum electroendosmotic flow, particularly in free zone electrophoresis and ECC techniques, where a large EOF is used to effectively lengthen the separation window of the analyte mixture.

For example, in zone electrophoresis with un-derivatized capillary tubes (i.e., having a negatively charged capillary walls), EOF toward the cathode can be established in opposition to the direction of migration of negatively charged analytes. Where the electrophoretic mobilities of such analytes are faster than the rate of EOF, the analytes are detected at the cathodic end in order of increasing electrophoretic mobility, as if the separation had been carried out in a static (non-moving) medium in a longer channel than actually used. More usually, the analytes migrate more slowly than the rate of EOF, so that the analytes are detected at the anodic end in order of decreasing mobility. In either case, the degree of analyte separation can therefore be enhanced.

With ECC techniques, a variety of separation formats can be used in which large EOF rates facilitate analyte separation, particularly in the context of electrically neutral or uncharged analytes. In ECC, the separation medium includes an additive, sometimes called "pseudo-phase", which is capable of forming transient complexes with the analytes during electrophoresis. In one approach, the additive has a net zero charge and migrates at the rate of EOF. In this case, charged analytes are separated based on a combination of electrophoretic mobility and differential interactions with the additive, usually with electrophoretic migration in the direction opposing the EOF. In a second approach, a charged additive is used having a mobility opposite the direction of EOF, usually to separate neutral analytes. Many suitable additives are known, such as cyclodextrin compounds and micelle-forming surfactants (Grossman et al., 1992, pp. 179–181 and 313–320).

Because of their dependencies on the magnitude of EOF, the methods above have been limited by the magnitude of EOF rate obtainable, pH limitations resulting from the bulk pKa of the silica surface, difficulties in establishing consistent EOF rates between successive runs, and inconsistencies among different capillary tubes. These problems are substantially reduced as a result of the present invention.

Example 8 illustrates use of the silicate reagent of the invention to achieve excellent and reproducible separations for a chiral mixture by means of a counter-current electrophoresis format. The chiral mixture, consisting of racemic atropine, "TROLOX" and 4-methyl-5-phenyl-2-oxazolidinone (MPO), was separated in capillary tubes from six different suppliers using a sulfonated β-cyclodextrin derivative as the pseudophase. As a control, DMSO marker was initially run alone in running buffer lacking cyclodextrin. As can be seen for the first five runs with DMSO marker alone (FIG. 9), use of silicate reagent affords high and consistent EOF rates of between about 4.7 and 5.0 ×$10^4$ $cm^2$/V.sec in all instances. Furthermore, this consistency extends to the separation of the chiral mixture (runs 6–10), wherein the six sample stereoisomers are all base-line resolved with very little change in mobility (FIG. 9). FIG. 10 illustrates continued run-to-run reproducibility, in terms of migration time, achieved with ten consecutive runs. As can be seen, the separations are complete within 14 minutes from the start time.

Example 9 illustrates the superior results provided by the invention as applied to the electrophoretic separation of a series of eight monosaccharide derivatives by micellar electrokinetic capillary chromatography (MECC). FIG. 11A shows the electropherogram obtained after the capillary tube was conditioned with NaOH solution alone. As can be seen, only three sample components (labeled A, B, and C in the figure) elute within the first 30 minutes of electrophoresis. However, once the capillary tube is treated with silicate reagent, all of the sample derivatives eluted within about 30 minutes, with the migration times of A, B, and C substantially reduced (FIG. 11B). FIG. 12 shows the migration times obtained in 17 consecutive runs with the derivatized saccharide mixture. As can be seen, the migration times are substantially consistent throughout the series. In fact, the migration times actually declined over successive runs, contrary to what would ordinarily be expected for MECC.

The enhanced and reproducible EOF rates provided by the method of the invention are also useful for transporting buffers, reagents, and samples in a miniature sample analysis system, such as formed in a glass or silica substrate in a microchip. Suitable methods for preparing such systems are described, for example, in articles by Jacobson et al. (1994a) and Manz et al. (1994), and references therein.

With reference to the fabrication method set forth in jacobson et al. (1994a), a miniature sample analysis system can be fabricated in the form of a microchip using standard photolithographic, chemical etching, and bonding techniques. A photomask is fabricated by sputtering chrome (e.g., with a thickness of 50 nm) onto a glass slide and ablating the desired capillary channels into the chrome film using a CAD/CAM excimer laser machining system. The channel design is then transferred onto a glass substrate using a positive photoresist. The channels are then etched into the substrate by immersion of the substrate in a dilute, stirred solution of $HF/NH_4$. To complete formation of the channels, a cover plate is bonded to the substrate over the etched channels by direct bonding (Jacobson et al., 1994b). Glass or plastic reservoirs are affixed to the substrate at appropriate channel termini with epoxy glue. Electrodes connected to a power supply are provided to control voltages across the channels.

The layout of an exemplary channel array in a microchip 50 for capillary electrophoresis is shown in FIG. 14. Separation channel 52 is linked at its inlet end with sample inlet 54, electrolyte inlets 55 and 56, reagent inlets 58 and 59, and sample outlet 60. At the outlet end of channel 52 are found outlet channels 62 and 64. Electrode ends 54a to 64a are placed at the distal termini of each of channels 54 to 64 to control the voltages across the respective channels. The channel array may include additional inlet and outlet channels depending on the needs of the particular application.

The dimensions of the channels are selected to assure efficient fluid flow and limit leakage between channels. By way of illustration, channel widths (as viewed from above the microchip) may range from about 20 to about 200 μm, and channel depths may be within a similar range. The reduction in EOF rate resulting from an increase in one dimension can be offset by reducing the other dimension (width versus depth). The lengths of the various channels may likewise vary, depending on the application. The length of the separation channel (e.g., 5–50 mm) is chosen to assure adequate analyte separation.

With continued reference to FIG. 14, the inlet and outlet channels 54 through 64 may be widened at a selected point from the separation channel to accomodate a greater volume of fluid. However, it will be appreciated that a defined portion of each channel nearest the respective junction with the separation channel should be narrow to allow adequate control over fluid flow.

In operation, the channel array is provided with the necessary sample, buffer and reagent fluids. Voltage potentials applied to the various channel ends are used to control the direction and rate of fluid flow via electro-osmotic flow (EOF). Passage of sample, as induced by appropriate voltage settings, through inlet channel 54 and outlet channel 60 creates a plug of sample in the portion of the separation channel between channels 54 and 60. To analyze a selected sample plug, the voltage settings are changed to induce fluid flow from electrolyte inlet 56, through separation channel 52, and exiting outlet channel 62 or 64. The sample may be detected and quantified using a detector suitably positioned along the separation channel or a selected outlet, or alternatively, using an external detector down-stream of one of the outlets. A number of miniature detectors for sample detection are available (e.g., Manz et al., 1994; Jacobson et al., 1994a,b, and references therein). To maintain high and reproducible flow rates, the silicate reagent is periodically passed through the separation channel, and other inlet and outlet channels as desired, to condition or regenerate the channel surface as discussed above.

In another general embodiment pertaining to electrophoretic separations, the silicate reagent of the invention is used to prepare a silica surface for chemical modification with a coating agent or polymerized matrix. Because treatment of a silica surface with silicate reagent leads to an increase in the number of surface silanol groups, the treated surface can bind a greater quantity of coating agent, whether by covalent or non-covalent means. The increased level of coating may also delay deleterious effects due to degradation of the coating during successive electrophoretic runs.

For example, cationic compounds containing a single or multiple positive charges per molecule (e.g., cetyltrimethylammonium bromide, tetradecyltrimetylammonium bromide, s-benzylthiouronium chloride, or putrescine) can be used to reduce or eliminate EOF, as in isoelectric focusing or zone electrophoresis, for example, and to prevent adsorption of cationic analytes. Polycationic coating agents are additionally useful for reversing the direction of EOF (Wiktorowicz, 1990; 1991), in which case it may be desirable to bind as many polycations as possible to maximize EOF. Covalent coating agents are used to suppress EOF, prevent binding of analyte or buffer components to the silica surface, and to anchor a polymerized matrices to the silica surface. In all of these examples, treatment of the initial silica surface with silicate reagent leads to improved results by increasing the quantity of coating bound, and by increasing the uniformity of the coating.

III. Chromatographic Applications

A. Chromatographic Separations with Underivatized Silica

In another aspect, the invention includes an improved method for capturing a nucleic acid on a silica particle. The improvement resides in the step of, prior to nucleic acid capture on the silica particle, contacting the silica particle with an alkaline aqueous solution containing a soluble silicate-monovalent metal complex in an amount effective to increase the acidity of the silica particle, leading to an increase in the binding capacity and/or binding affinity of the silica particle for the nucleic acid. The increased binding capacity is greater than that which would be obtained using an otherwise identical solution lacking said silicate.

In practicing the method, silica particles prepared by conventional means may be used which are effective to tightly bind nucleic acids in the presence of a suitable chaotrophic agent. Suitable silica particles are available from a number of commercial suppliers, including Aldrich Chem. Co., Fluka Chem. Co., and Sigma Chem. Co. Commercial cartridges and accessories utilizing silica gel or diatomaceous earth for binding nucleic acids are available from Perkin-Elmer, Applied Biosystems Division (Foster City, Calif., "BASEBINDER" reagent) and Promega Corp. (Madison, Wisc., "WIZARD" miniprep system), for example.

Size-fractionated silica particles for use in the method may be prepared by suspending commercial silicon dioxide particles in demineralized water (water:$SiO_2$~10:1) and allowing the particles to sediment over 24 h at room temperature in a glass cylinder). The majority of the supernatant is removed, and sedimentation is repeated. Following removal of most of the supernatant by aspiration, the pH of the suspension is titrated to pH 2 with concentrated HCl and stored for use. A more detailed description of this process can be found in Boom et al. (1990). For binding larger amounts of nucleic acids, a suspension of diatomaceous earth can be prepared by adding water (50 mL) and HCl (500 μL, 32% wt/vol) to high-purity, analytical grade "CELITE" and storing at room temperature. The suspensions may be autoclaved to destroy adventitious nucleic acids. For the following discussion, "silica particles" is intended to encompass diatomaceous earth particles as well.

The nucleic acid-containing sample is prepared from blood, urine, eukaryotic or prokaryotic cells, or another source, by mixing with a buffer containing a chaotrophic agent, and optionally a buffer, EDTA, and denaturant (e.g., TRITON X-100 or dimethylformamide), as necessary. The chaotrophic agent is one which contains a small monovalent or divalent cation, such as sodium iodide, sodium acetate, guanidinium thiocyanate, or guaninidium chloride, which mediates binding of nucleic acids to the silica particles. An exemplary lysis buffer ("L6") containing guanidinium thiocyanate, Tris buffer pH 6.4, EDTA and TRITON X-100 is described in Boom et al. (1990).

Prior to binding sample, the silica particles are contacted or washed with a silicate reagent of the type above, under conditions effective to increase the acidity of the silica surface of the particles, providing enhanced binding affinity for nucleic acids. After the wash step is complete, the silica particles are washed with buffer to remove the silicate reagent, in preparation for sample addition.

After treatment with alkaline silicate reagent of the invention, the silica particles may be used in the form of a suspension which is contacted with the nucleic acid sample by mixing. In one protocol (Boom et al., 1990), lysis buffer (900 μL) is added to silica particle suspension (40 μL) in an Eppendorf tube (1.5 mL volume) and vortexed to homogeneity. A 50 μL of blood or urine is added and the vessel is immediately vortexed for 5 seconds. After sitting for 10 minutes at room temperature, the vessel is vortexed again. The mixture is then pelleted by centrifugation (15 s, 12000× g) and the supernatant is removed by suction. The pellet is then washed with TE buffer (10 mM Tris, 1 mM EDTA, pH 8) 70% aqueous ethanol, and acetone, followed by drying of the particles using a heat block (56° C., 10 minutes). The purified nucleic acids are eluted from the particles by adding TE buffer, vortexing briefly, incubating at 56° C. for 10 minutes, vortexing again, and centrifugation for 2 minutes at 12,000×g. The supernatant, which contains the nucleic acids of interest, is collected and stored. Other protocols for sample preparation may also be used, the above being merely illustrative.

The silica particles may also be used in a column or cartridge format, wherein reagents and nucleic acid sample are passed through the column bed in the general sequence noted above. The nucleic acids are then eluted from the particles using water or other low ionic strength buffer.

The invention also contemplates kits for use in the method above, which include one or more containers of the silicate solution of the invention, silica particles, and suitable buffers and wash reagents.

B. Preparation of Derivatized Silica for Liquid Chromatography

In another embodiment relating to chromatographic applications, the silicate solution of the invention may be used to activate silica support materials for use in liquid chromatography (LC) or gas chromatography (GC) prior to covalent modification with a stationary phase reagent in the case of LC, or with a deactivating agent in the case of GC.

In the case of LC applications, the treatment of an underivatized silica surface (e.g., a silica particle treated with silicate solution is effective to increase the density of reactive silanol groups on the surface which are reactive toward a selected stationary phase. The increased density of reactive silanol groups thus leads to an increase in density of stationary phase molecules on the surface, with a consequent increase in theoretical plates and a reduction in the number of sites in the silica surface that are susceptible to hydrolysis during sample separation. This latter feature is desirable because hydrolysis of Si-O-Si bonds to produce new silanol groups on the silica surface during sample separation can lead to deleterious changes in the affinity characteristics of the stationary phase over time. For example, an increase in silanol groups can lead to an increase in irreversible binding of analytes or buffer components to the solid phase, or alternatively, to a decreased affinity if the silanol groups impede such binding.

The silicate treatment step of the invention finds application in preparing a wide variety of stationary phases for LC and GC, wherein known methods for preparing such phases are simply modified to include treatment of an underivatized silica surface with the alkaline silicate solution of the invention, prior to derivatization with a selected stationary phase reagent or blocking agent.

For preparing a particulate silica sorbent (silica particles) for use in LC, silica particles having a desired average diameter and pore size may be prepared by standard methods, or may be obtained from commercial sources as already described above (see also Henry, 1991). For high pressure liquid chromatography (HPLC) applications, silica particles having diameters smaller than 10 μm are used, and preferably less than about 1 μm, whereas for low pressure or batch methods, particles with larger diameters are generally used.

In a typical procedure for preparing a particulate sorbent for LC in accordance with the invention, porous particulate silica, e.g., as a bulk powder, is washed with concentrated acid (e.g., 6N HCl) to remove most metallic impurities and hydroxylates on the surface. This acid wash step may be carried out at elevated temperature. The silica is then thoroughly washed with pure water until most residual acid and chloride ions have been removed. The wetted silica is then dried by heating, typically at about 160° C., and usually for 4–20 hours.

The silica surface is then contacted with an alkaline silicate solution prepared as above for a time and at a concentration sufficient to increase the surface acidity of the silica surface by a selected amount. Generally, the conditions used in this step may be optimized through studies using a range of contact times and silicate concentrations until the desired results are obtained. The change in acidity may be assessed by silicon NMR (nuclear magnetic resonance), titration methods, EOF measurements, or based on the resultant increase in density of stationary phase. The silica is then washed with water to remove residual silicate reagent and is then dried, typically under reduced pressure and/or elevated temperature to dehydrate the surface.

The silica is next reacted with a selected stationary phase reagent under reaction conditions known in the art. Typically, the stationary phase reagent is an organosilane compound, such as a mono- or trialkoxy or trichloro alkyl or aryl silane. The alkyl or aryl group may be any of a variety of hydrocarbons, most commonly octadecyl. Such compounds are not inclusive but merely illustrate the types of stationary phase reagents that can be used. For example, descriptions of known stationary phase reagents and their uses can be found in Unger (1990), Unger et al. (1989), Majors (1994), Anderson (1995), Hearn (1991), and Snyder (1979).

The resultant silica particles are then packed in a column and their separation, stability and reproducibility properties may then be assessed by iterative runs with a sample mixture or a standard.

C. Improved Coatings for Gas Chromatography

For preparing an improved GC stationary phase, typically referred to as a liquid stationary phase, in accordance with the invention, a treatment step with the alkaline silicate solution of the invention is incorporated into an otherwise standard method for preparing a coated GC column. A discussion of prior art methods for preparing a wide variety of coated GC columns can be found in Grob (1986).

In practicing the present invention, a silica capillary tube (preferably a fused silica capillary tube) is usually acid-washed to remove surface bound cationic impurities such as metal ions. Usually, this can be accomplished by flushing an aqueous solution of 2% HCl through the capillary tube, sealing the tube at its ends, and heating it at elevated temperature (e.g., 220° C.) for a selected time (e.g., 1–24 hours).

The capillary tube is then unsealed and flushed extensively with water to remove the acid. The capillary tube is then flushed with alkaline silicate solution of the type described above for a time sufficient to increase the surface acidity of the capillary wall as before. After this, the capillary tube is flushed with water, followed by a stream of inert dry gas at elevated temperature to dehydrate the surface.

In an alternative embodiment, treatment with the alkaline silicate solution precedes the acid wash step, in which case the tube is dried by gas stream after the acid-heat step.

In one embodiment, the dried, silicate-treated tube is then deactivated with a blocking agent, typically an organosilane compound such as dimethyl dichlorosilane or octamethyltetracyclosiloxane, to block surface silanol groups and render the silica surface hydrophobic. The inner surface of the capillary is then coated with a liquid phase, typically a silicone oil, to impart the desired absorbent properties to the capillary wall. Usually, the oil is immobilized by in situ polymerization by known methods (e.g., Grob, 1986, and references therein).

In a second embodiment, the dried, silicate-treated tube is reacted directly with a liquid stationary phase reagent which covalently binds to the silica surface, without the need for preliminary surface deactivation. After reaction with the liquid stationary phase reagent is complete, the surface may be further treated with a deactivating reagent to cap remaining silanol sites.

The alkaline silicate solution used in preparing a silica capillary surface as above is effective to improve the efficiency of the deactivation step as well as the degree of binding of stationary phase to the surface. In addition, where the liquid stationary phase is itself covalently bound to the silica surface, with or without a subsequent deactivation step, treatment with the silicate solution again increases the density of the liquid stationary phase bound to the silica surface.

The invention also contemplates pretreatment of a silica surface with the alkaline silicate reagent where the liquid stationary phase has a high, non-covalent affinity for silanol groups on the silica surface.

The features and advantages of the invention will be further appreciated from the following examples, which are intended to illustrate but not limit the scope of the invention.

EXAMPLES

General All experiments were conducted at ambient temperature (about 20°–25° C.) unless indicated otherwise. All chemical reagents were reagent grade or better, and were obtained from readily available commercial sources. Unless otherwise indicated, capillary electrophoresis was carried out using underivatized fused silica capillary tubes 72 cm in length, 50 μm inner diameter, in a Capillary Electrophoresis System from Perkin-Elmer Applied Biosystems Division (Foster City, Calif.), Model 270A-HT, equipped with UV detector, inlet to detector=50 cm, anode at the inlet end, at a run temperature of 30° C. Buffers and rinse solutions were passed through the column by vacuum injection at a pressure difference of 20 inches of mercury. Sample solutions were loaded by vacuum injection at a pressure difference of 5 inches of mercury, with a load time of 1 to 5 seconds.

Example 1

EOF as Function of Silicate Concentration

Aliquots of a stock solution of sodium silicate (27% $SiO_2$/14% NaOH, from Aldrich Chem. Co., Prod. No. 33,844–3) were diluted to final concentrations of 0.03, 0.05, 0.08, 0.1, 0.2, 0.4, and 0.8 weight percent $SiO_2$ (500 μL final volume) in 270HT polypropylene 1.5 mL vials equipped with septa (PerkinElmer Applied Biosystems Division, Prod. Nos. 0603-0008 and -0009). The concentration of NaOH was maintained at 100 mM by adding an appropriate amount of NaOH stock solution.

For this study, a new capillary tube was pre-conditioned as follows: wash with 1M NaOH for 20 minutes; water for 3 minutes; silicate solution in 100 mM NaOH for 20 minutes; and water for 3 minutes.

Prior to each electrophoretic run, the following prerun rinse cycle was performed: wash with silicate solution for 3 minutes; water for 0.5 minutes; 20 mM sodium acetate buffer, pH 4.5, for 5 minutes. DMSO marker (dimethyl sulfoxide, 0.05 or 0.1% in water) was loaded by vacuum injection, and electrophoresis was commenced. EOF values were determined based on the time taken for the DMSO peak to reach the detector. As a control, 100 mM NaOH was used in place of silicate solution in the pre-run cycle. In subsequent electrophoretic runs, silicate solutions of increasing silicate concentrations were used. Runs were performed in triplicate for each silicate concentration before changing to the next highest silicate concentration in the conditioning step. All runs were performed using the same capillary tube. The results are shown in FIG. 1, with each point representing the average of data collected in triplicate.

Example 2

Metasilicate Versus Silicate

A commercial solution of sodium silicate (27% $SiO_2$/14% NaOH, Fluka Chem. Co. (Ronkonkom, N.Y.), Prod. No. 71957) was diluted to a final concentration of 0.25% $SiO_2$ in 100 mM NaOH. A solution of solubilized anhydrous solid sodium metasilicate ($Na_2SiO_3$, Aldrich, Prod. No. 30,781–5) of equivalent $SiO_2$ and NaOH concentrations was also prepared.

A new capillary tube was pre-conditioned by washing with 1N NaOH for 30 minutes, and then water for 3 minutes. Pre-run rinse cycles and measurement of EOF were performed as in Example 1. The results for seven consecutive runs (including a non-silicate control in run number 0) are shown in FIG. 2.

Example 3

$SiO_2/Na_2O$ Ratio

Sodium silicate solutions containing three different concentrations of sodium silicate (0.2, 0.4, and 0.6% $SiO_2$) and a range of NaOH concentrations (0.25 to 200 mM) were prepared. For this study, a new capillary tube was preconditioned as in Example 1, using as silicate reagent a solution containing 0.2% $SiO_2$ and the lowest concentration of NaOH. Prior to each electrophoresis run, the pre-run cycle from Example 1 was performed. EOF mobilities were obtained in triplicate with DMSO marker for each NaOH concentration (starting with the lowest) before changing to silicate solution containing the next highest NaOH concentration. After the last of the 0.2% $SiO_2$ solutions had been tested, the conditioning procedure from Example 1 was carried out, followed by electrophoresis as above using the 0.4% $SiO_2$ solutions (lowest NaOH concentration first). The solutions containing 0.6% $SiO_2$ were tested last in the same manner, after the capillary tube had first be conditioned as in Example 1. The measured mobilities are shown in FIG. 3.

Example 4

Effect of SDS on EOF

A. As Function of Silicate Concentration

Figure 4B:
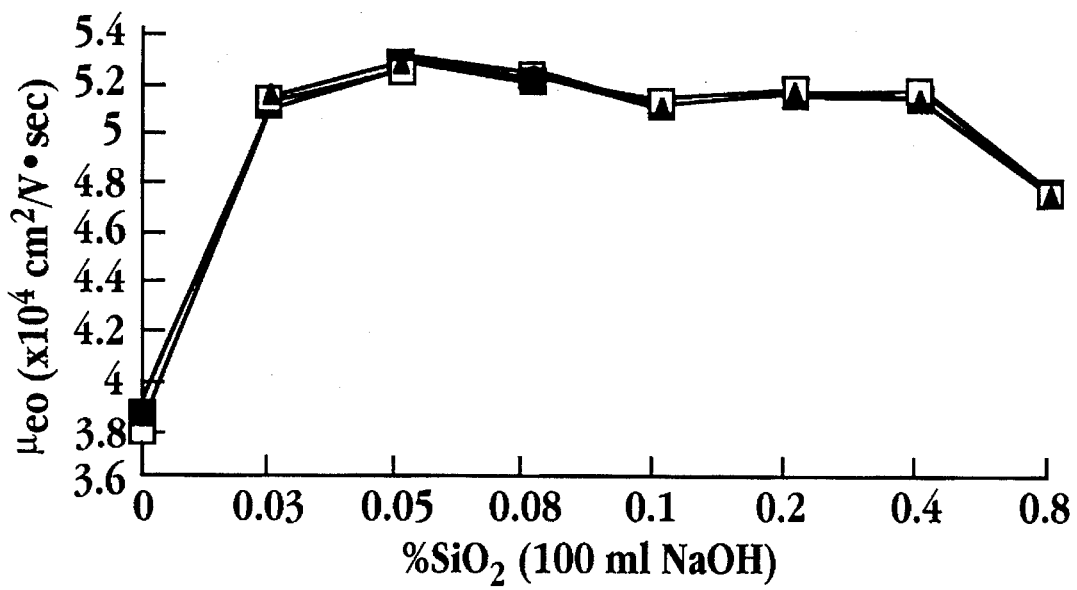

In this study, the procedure for measuring EOF mobility from Example 1 was repeated except that the running buffer was a Tris-phosphate buffer containing 30 mM phosphate, ~60 mM Tris, and 0, 50, or 100 mM SDS, pH 7.4. A new capillary tube was used for each SDS concentration. Data were collected in triplicate, from lowest to highest silicate concentration. Prior to switching to the next silicate concentration, the capillary tube was conditioned by washing with water for 3 minutes, the next silicat solution for 20 minutes, water for 3 minutes, buffer for 20 minutes, and water for 3 minutes. Each electrophoresis run was preceded by a pre-run cycle consisting of washing with silicate solution for 2.5 minutes, water for one minute, and running buffer for 5 minutes. The results are shown in FIGS. 4A–4B (for 0 and 50 mM SDS, respectively). The results for 100 mM SDS (not shown) were similar to those for 50 mM SDS.

B. As Function of NaOH Concentration

Sodium silicate solutions containing two different concentrations of sodium silicate (0.2 and 0.4% $SiO_2$) and a range of NaOH concentrations (~40–200 mM) were prepared. For each silicate concentration tested, a new capillary tube was preconditioned as in Example 1. Each data point was run in triplicate. Electrophoresis runs with DMSO marker were preceeded by a pre-run cycle as in Example 1 using successive silicate solutions of increasing NaOH concentration, except that the wash with silicate solution was for 20 minutes rather than 3 minutes, and the running buffer was the Tris-phosphate (50 mM SDS) from Example 4A, rather than the sodium acetate buffer from Example 1. The measured EOF mobilities are shown in FIG. 5A and 5B, respectively.

Example 5

Length of Exposure to Silicate Reagent

Figure 6:
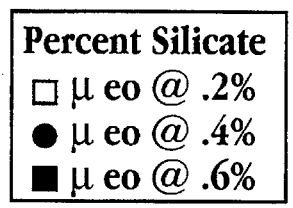
FIG. 6 shows a plot of EOF mobility measured in 20 mM sodium acetate running buffer, pH 4.5, by CE as a function of time of exposure of the capillary tube to silicate reagent (0.25% $SiO_2$/100 mM NaOH); lower trace, 10 minute exposure; middle trace, 20 minute exposure; upper trace, 30 minute exposure.
Figure 6:
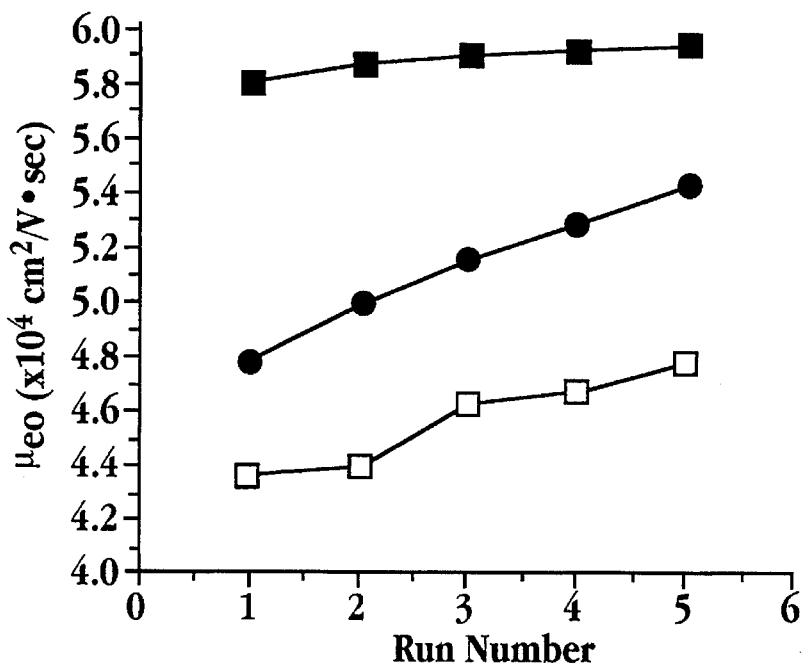

A new capillary tube was conditioned by washing with water for 3 minutes, followed by 1N NaOH for a selected incubation time ("X") of 10, 20, or 30 minutes. The column was then treated with a pre-run cycle involving the following steps: wash with water for 3 minutes; silicate solution for "X" minutes (0.25% $SiO_2$ in 100 mM NaOH); water for 3 minutes; and 20 mM sodium acetate pH 4.5 buffer for 5 minutes. For each wash time X, EOF measurements were obtained with DMSO marker for five consecutive runs. A separate capillary tube was used for each value of X. The results are shown in FIG. 6.

Example 6

Conditioning with Silicate Reagent Versus Aqueous Sodium Hydroxide (Chiral Separation)

Electrophoretic mobilities of a neutral marker (DMSO) and three charged compounds were measured in 20 consecutive runs following preconditioning of capillary tubes with 100 mM NaOH with or without silicate reagent (0.2% $SiO_2$) as follows.

For runs which omitted exposure to silicate reagent, a new capillary tube was conditioned as follows: wash with 1N NaOH for 30 minutes; water for 3 minutes; 100 mM NaOH for 30 minutes; water for 3 minutes; and sodium acetate buffer, pH 4.5, for 10 minutes. Each electrophoresis run was preceded by the pre-run cycle from Example 1 using 100 mM NaOH. The sample mixture to be resolved contained DMSO, "TROLOX" atropine and 4-methyl-5-phenyl-2-oxazolidinone (MPO).

For runs which included treatment with silicate reagent, the same conditioning and pre-run procedures were used as above with a new capillary tube, except that in both the conditioning and pre-run cycles, 0.2% $SiO_2$/100 mM NaOH was used in place of the 100 mM NaOH solution. The results are shown in FIG. 7.

Example 7

Average pKa of Capillary Surface

Average bulk pKa values for the inner wall of a fused silica capillary tube were estimated after preconditioning with different silicate concentrations as follows.

The following electrophoresis running buffers were prepared: sodium citrate, pH 2.5; sodium acetate, pH 4.5; BES (N,N-bis[2-hydroxyethyl]-2-aminoethanesulfonic acid), pH 6.0 and 7.0; bicine (N,N-bis[2-hydroxyethyl]glycine), pH 8.0; CHES (2-[N-cyclohexylamino]ethanesulfonic acid), pH 9.0; and CAPS (3-cyclohexylamino-1-propanesulfonic acid), pH 10.0 and 11.0. The conductivity of each buffer solution was adjusted to 2800–2900 μmhos with NaCl.

A new capillary tube was preconditioned by washing with 1N NaOH for 20 minutes, followed by water for 3 minutes. Each electrophoresis run was preceded by the pre-run cycle from Example 1, starting first with a "control silicate solution" consisting only of 100 mM NaOH, and the pH 11 running buffer. The mobility at each pH was measured in triplicate prior to changing to the running buffer with the next lowest pH.

After the mobility had been measured for the last run buffer (pH 2.5) with the "control silicate solution", the column was reconditioned by washing with 1N NaOH for 20 minutes and water for 3 minutes as before. Mobilities were then measured with the next silicate solution (0.5% $SiO_2$), starting with the highest pH running buffer and successively changing to running buffers of lower pH. Each run was preceded by a pre-run cycle as above, where the 100 mM NaOH was replaced with silicate reagent. Mobility data for the 0.1% and 0.3% silicate solutions were obtained similarly, subject to preconditioning of the column with 1N NaOH and water as above.

After data had been collected for the last run with the 0.3% silicate solution, the column was reconditioned as follows: wash with 1N NaOH for 20 minutes; water for 3 minutes; 0.3% SiO$_2$/100 mM NaOH solution for 20 minutes; and water for 3 minutes. This was followed by the same pre-run cycle as above, using the 0.3% SiO$_2$/100 mM NaOH solution in the first step of each pre-run cycle. Mobility data were then measured using this pre-run cycle as above, starting with pH 11 running buffer. The results are shown in FIG. 8.

Example 8

Migration Time Reproducibility With Capillary Tubes from Different Suppliers

Fused silica capillary tubes (72 cm length, 50 µm inner diameter) were purchased from Polymicro Technologies Inc. (Phoenix, Ariz.), Hewlett-Packard (Wilmington, Del.), Scientific Glass Engineering, Inc. (Austin, Tex.), Chrompack Inc. (Raritan, N.J.), and Quadrex Corp. (New Haven, Conn.).

The capillary tubes were preconditioned with silicate reagent as described in Example 5, using 0.25% SiO$_2$/100 mM NaOH as silicate reagent with an exposure time (X) of 30 minutes. The pre-run cycles were also as in Example 5. The first five electrophoresis runs were with DMSO marker alone, and the next five runs were carried out with the chiral sample mixture from Example 6, using 20 mM sodium acetate buffer, pH 4.5, additionally containing 5 mM sulfobutylether-derivatized β-cyclodextrin, as running buffer. The measured mobilities are shown in FIGS. 9A–9F. The run-to-run reproducibility of migration times as measured in 10 consecutive runs is shown in FIG. 10.

Example 9

Run-to-Run Reproducibility: MECC of Monosaccharide Mixture

For resolving a mixture of monosaccharide derivatives, a new capillary tube (92 cm length×50 µm inner diameter) was preconditioned without silicate reagent as follows: wash with water for 3 minutes; 1N NaOH for 30 minutes; water for 3 minutes; 100 mM NaOH for 30 minutes; water for 3 minutes; running buffer for 30 minutes (Tris/phosphate from Example 4A, pH 7.4, containing 50 mM SDS), and water for 3 minutes.

The sample mixture consisted of eight monosaccharides labeled with 1-phenyl-3-methyl-2-pyrazolin-5-one (PMP) which eluted in the following order: (1) free-PMP, (2) PMP-mannose, (3) PMP-talose, (4) PMP-glucose, (5) PMP-glucosamine, (6) PMP-xylose, (7) PMP-galactose, (8) PMP-fucose, and (9) PMP-galactosamine.

For electrophoresis runs in this study, a voltage of 27 kV was applied, capillary temperature was 30° C., and the absorbance wavelength for detection was 245 nm.

Prior to the first electrophoresis run, the capillary tube was subjected to the following pre-run cycle: wash with 100 mM NaOH for 2.5 minutes; water for 2 minutes; running buffer for 5 minutes. FIG. 11A shows the electropherogram obtained in the first run (first 30 minutes only).

Following the first electrophoresis run, the capillary tube was subjected again to the same pre-conditioning and pre-run procedures except that the 100 mM solution of NaOH additionally included silicate reagent (0.34% SiO$_2$). The first electropherogram obtained under these conditions is shown in FIG. 11B.

A total of 17 consecutive electrophoresis runs were performed as in the preceding paragraph with a new capillary tube, where each run was preceded by the pre-run procedure noted therein. A plot of the migration times obtained is shown in FIG. 12.

Although the invention has been described with respect to particular embodiments, it will be appreciated that various changes and modifications can be made without departing from the invention.

It is claimed:

1. A method for increasing electroosmotic flow of a silica surface, comprising:

providing one or more silica surfaces defining an electrophoretic channel, contacting said surface(s) with an alkaline aqueous solution containing a soluble silicate-monovalent metal complex in an amount effective to increase the acidity of the silica surface(s), as evidenced by a reduction in the average bulk pKa of said surface(s), wherein the achieved increase in acidity is greater than would be obtained using an otherwise identical solution lacking said silicate.

2. The method of claim 1, wherein said monovalent metal in said complex is selected from the group consisting of Li$^+$, Na$^+$, and K$^+$.

3. The method of claim 2, wherein the monovalent metal is Na$^+$.

4. The method of claim 2, wherein said solution has a SiO$_2$ concentration from 0.05 to 5 weight %.

5. The method of claim 4, wherein the SiO$_2$ concentration is from 0.05 to 1.0 weight %.

6. The method of claim 2, wherein the monovalent metal is Li$^+$.

7. The method of claim 2, wherein the monovalent metal is K$^+$.

8. The method of claim 2, wherein said electrophoretic channel is formed by a capillary tube.

9. The method of claim 1, wherein prior to said contacting, the silica surface(s) are contacted with an aqueous solution of MOH having a pH greater than 11, where M is selected from the group consisting of Li$^+$, Na$^+$, and K$^+$.

10. An electrophoresis method for analysis of one or more analytes in a sample, comprising:

providing a silica surface which defines an electrophoretic channel having an inlet end and an outlet end, contacting said surface with an alkaline aqueous solution containing a soluble silicate-monovalent metal complex in an amount effective to increase the acidity of the silica surface, wherein the achieved increase in acidity is greater than would be obtained using an otherwise identical solution lacking said silicate, replacing said solution with a selected running buffer, loading a sample containing one or more analytes into the inlet end of the channel, immersing the ends of the channel in anodic and cathodic reservoirs each containing an electrolyte solution, applying an electric field across the ends of the channel under conditions effective to induce said analyte(s) to migrate toward the outlet end of the tube, and detecting said one or more analytes.

11. The method of claim 10, wherein said monovalent metal in said complex is selected from the group consisting of $Li^+$, $Na^+$, and $K^+$.

12. The method of claim 11, wherein the monovalent metal is $Na^+$.

13. The method of claim 11, wherein said solution has a $SiO_2$ concentration from 0.05 to 5 weight %.

14. The method of claim 10, wherein prior to said contacting, the silica surface(s) are contacted with an aqueous solution of MOH having a pH greater than 11, where M is selected from the group consisting of $Li^+$, $Na^+$, and $K^+$.

15. The method of claim 10, wherein said electrophoretic channel is formed by a capillary tube.

16. The method of claim 11, wherein the monovalent metal is $Li^+$.

17. The method of claim 11, wherein the monovalent metal is $K^+$.

18. The method of claim 13, wherein the $SiO_2$ concentration is from 0.05 to 1.0 weight %.

* * * * *